United States Patent
Emiru et al.

(10) Patent No.: US 9,956,153 B2
(45) Date of Patent: May 1, 2018

(54) ANTIMICROBIAL FOAMING COMPOSITIONS CONTAINING CATIONIC ACTIVE INGREDIENTS

(71) Applicant: Ecolab USA Inc., St. Paul, MN (US)

(72) Inventors: Hilina Emiru, Rosemount, MN (US); Cheryl A. Littau, Apple Valley, MN (US); Joseph R. Wegner, Falcon Heights, MN (US); Daniel E. Pedersen, Cottage Grove, MN (US); Mai Le, Maplewood, MN (US); Amanda L. Wessinger, Hastings, MN (US)

(73) Assignee: Ecolab USA Inc., Saint Paul, MN (US)

( * ) Notice: Subject to any disclaimer, the term of this patent is extended or adjusted under 35 U.S.C. 154(b) by 158 days.

(21) Appl. No.: 14/449,895

(22) Filed: Aug. 1, 2014

(65) Prior Publication Data

US 2016/0030315 A1     Feb. 4, 2016

(51) Int. Cl.
| | | |
|---|---|---|
| A61K 8/41 | (2006.01) | |
| A61K 8/04 | (2006.01) | |
| A61Q 19/10 | (2006.01) | |
| A61K 8/86 | (2006.01) | |
| A61K 8/34 | (2006.01) | |
| A61K 8/42 | (2006.01) | |
| A61K 8/37 | (2006.01) | |
| A61K 8/40 | (2006.01) | |
| A61Q 17/00 | (2006.01) | |
| A61K 9/00 | (2006.01) | |
| A61K 47/10 | (2017.01) | |
| A61K 47/14 | (2017.01) | |
| A61K 9/12 | (2006.01) | |
| A01N 33/12 | (2006.01) | |

(52) U.S. Cl.
CPC .............. *A61K 8/416* (2013.01); *A01N 33/12* (2013.01); *A61K 8/046* (2013.01); *A61K 8/345* (2013.01); *A61K 8/375* (2013.01); *A61K 8/40* (2013.01); *A61K 8/42* (2013.01); *A61K 8/86* (2013.01); *A61K 9/0014* (2013.01); *A61K 9/122* (2013.01); *A61K 47/10* (2013.01); *A61K 47/14* (2013.01); *A61Q 17/005* (2013.01); *A61Q 19/10* (2013.01)

(58) Field of Classification Search
None
See application file for complete search history.

(56) References Cited

U.S. PATENT DOCUMENTS

| | | |
|---|---|---|
| 4,567,174 A | 1/1986 | Edwards et al. |
| 4,764,365 A | 8/1988 | Boothe et al. |
| 5,188,756 A | 2/1993 | Baker |
| 5,234,618 A | 8/1993 | Kamegai |
| 5,376,686 A | 12/1994 | Ishikawa et al. |
| 5,415,814 A | 5/1995 | Ofosu |
| 5,417,893 A | 5/1995 | Ofosu |
| 5,653,970 A | 8/1997 | Vermeer |
| 5,707,959 A | 1/1998 | Pancheri |
| 5,719,113 A | 2/1998 | Fendler et al. |
| 5,756,446 A | 5/1998 | Bator |
| 6,057,274 A | 5/2000 | Bator |
| 6,221,828 B1 | 4/2001 | Matsuo |
| 6,323,171 B1 | 11/2001 | Fonsny |
| 6,340,663 B1 | 1/2002 | Deleo et al. |
| 6,384,004 B2 | 5/2002 | McCandlish |
| 6,387,866 B1 | 5/2002 | Mondin |
| 6,395,691 B1 | 5/2002 | Tsaur |
| 6,432,907 B1 | 8/2002 | Skold |
| 6,616,922 B2 | 9/2003 | Taylor et al. |
| 6,680,286 B1 | 1/2004 | Kawaguchi et al. |
| 6,730,654 B2 | 5/2004 | Godfroid et al. |
| 6,762,162 B1 | 7/2004 | Valpey, III et al. |
| 6,764,989 B1 | 7/2004 | Huish |
| 6,846,492 B2 | 1/2005 | Haap et al. |
| 6,946,786 B2 | 1/2005 | Patel |
| 6,881,710 B1 | 4/2005 | O'Lenick, Jr. et al. |
| 6,906,018 B1 | 6/2005 | Patel |
| 6,906,023 B1 | 6/2005 | Patel |
| 6,923,988 B2 | 8/2005 | Patel et al. |
| 6,977,082 B2 | 12/2005 | Seitz, Jr. et al. |
| 7,084,129 B1 | 8/2006 | Smith et al. |
| 7,112,559 B1 | 9/2006 | Mayhall et al. |

(Continued)

FOREIGN PATENT DOCUMENTS

| | | |
|---|---|---|
| EP | 1669061 B1 | 6/2006 |
| EP | 1669061 B9 | 3/2010 |

(Continued)

OTHER PUBLICATIONS

CCI, "Cola Liquid", 2 pages. Mar. 31, 2013.
CCI, "Poly Suga Quat Series—Natural, Green Conditioning Surfactants", 4 pages. Dec. 31, 2007.
CCI, "Safety Data Sheet, Cola Liquid DC", 5 pages. Mar. 12, 2012.
CCI, "Safety Data Sheet, Cola Liquid DL", 5 pages. Mar. 12, 2012.
CCI, "Safety Data Sheet, Cola Liquid DM", 5 pages. Mar. 12, 2012.
CCI, "Safety Data Sheet, Cola Liquid DO", 5 pages. Feb. 21, 2013.
CCI, "Tea Tree Shampoo with Conditioning", 1 pages, last updated Jul. 19, 2006.
CCI, "Technical Data Sheet, Cola Liquid BL, Liquid Lauramide MIPA", 1 page. Dec. 31, 2013.
Claesson, Per M., "Sugar Surfactants", Royal Institute of Technology and Institute for Surface Chemistry, pp. 4909-4925. Dec. 31, 2002.

(Continued)

*Primary Examiner* — Jessica Worsham
(74) *Attorney, Agent, or Firm* — McKee, Voorhees & Sease, PLC

(57) ABSTRACT

The antimicrobial foaming composition of the present invention comprises a cationic active ingredient, a cationic compatible surfactant, a foam booster, a foam structure enhancing agent, dermal adjuvants, and a carrier. The present antimicrobial compositions are free of the antimicrobial agents triclosan (i.e., 2,4,4'-trichloro-2'hydroxy-diphenylether) and lower alcohols. They are also free of anionic surfactants. The foaming compositions have rapid cidal activity, provide stable, copious foam, and exhibit enhanced tissue (e.g. skin) compatibility.

19 Claims, 5 Drawing Sheets

(56) References Cited

U.S. PATENT DOCUMENTS

| | | |
|---|---|---|
| 7,163,914 B2 | 1/2007 | Gluck |
| 7,179,779 B1 | 2/2007 | Hauser |
| 7,250,392 B1 | 7/2007 | Leonard |
| 7,345,015 B1 | 3/2008 | Kong et al. |
| 7,374,779 B2 | 5/2008 | Chen et al. |
| 7,501,387 B2 | 3/2009 | Aihara |
| 7,507,399 B1 | 3/2009 | O'Lenick, Jr. |
| 7,544,649 B2 | 6/2009 | Aihara |
| 7,547,672 B2 | 6/2009 | Zaki |
| 7,709,430 B2 | 5/2010 | Mizushima |
| 7,795,000 B2 | 9/2010 | Podtburg et al. |
| 7,897,553 B2 | 3/2011 | Heiler |
| 8,193,136 B2 | 6/2012 | Taylor et al. |
| 8,388,991 B2 | 3/2013 | Sondgeroth et al. |
| 8,445,616 B2 | 5/2013 | Bergeron et al. |
| 8,541,454 B2 | 9/2013 | Behrends et al. |
| 8,598,106 B2 | 12/2013 | Schwarz et al. |
| 8,658,586 B2 | 2/2014 | Karagianni et al. |
| 8,709,466 B2 | 4/2014 | Coady et al. |
| 2002/0155978 A1 | 10/2002 | Man |
| 2002/0183233 A1 | 12/2002 | Shuman |
| 2003/0074742 A1 | 4/2003 | Perry |
| 2004/0136940 A1 | 7/2004 | Lazarowitz |
| 2005/0000030 A1 | 1/2005 | Dupont |
| 2005/0176614 A1 | 8/2005 | Soldanski |
| 2005/0215461 A1 | 9/2005 | Gluck et al. |
| 2006/0142174 A1 | 6/2006 | Fukuda |
| 2008/0161268 A1 | 7/2008 | Yen et al. |
| 2008/0209645 A1 | 9/2008 | Carrillo |
| 2009/0069436 A1 | 3/2009 | MacGregor |
| 2010/0081596 A1 | 4/2010 | Rong |
| 2011/0092405 A1* | 4/2011 | Ryklin ............ A61K 8/375 510/123 |
| 2012/0070341 A1 | 3/2012 | Eder et al. |
| 2012/0071438 A1 | 3/2012 | Pedersen et al. |
| 2012/0148751 A1 | 6/2012 | Herdt et al. |
| 2013/0035396 A1 | 2/2013 | Moen et al. |
| 2014/0171513 A1 | 6/2014 | Seidling et al. |

FOREIGN PATENT DOCUMENTS

| | | |
|---|---|---|
| WO | 9606619 | 3/1996 |
| WO | 0107547 | 2/2001 |
| WO | 2006013315 | 2/2006 |
| WO | 2009029046 | 3/2009 |
| WO | 2009050447 | 4/2009 |
| WO | 2013061082 | 5/2013 |
| WO | 2013148247 | 10/2013 |
| WO | 2014090959 | 6/2014 |

OTHER PUBLICATIONS

Coots, Robert J., et al., "New, Natural-based Quaternary Conditioners for Personal Care Applications", 9 pages. Jan. 31, 2009.

Simoes, Manuel, et al., "Action of a cationic surfactant on the activity and removal of bacterial biofilms formed under different flow regimes", Water Research 29, pp. 478-486. Sep. 21, 2004.

Viscardi, Guido, et al., "Synthesis and Surface and Antimicrobial Properties of Novel Cationic Surfactants", J. Org. Chem. 65, pp. 8197-8203. Oct. 28, 2000.

EP 1669061 B1 and B9, Merz Pharma GmbH—English Translation and Abstract, 16 pages. Jun. 14, 2006.

\* cited by examiner

ANTIMICROBIAL FOAMING COMPOSITIONS CONTAINING CATIONIC ACTIVE INGREDIENTS

FIELD OF THE INVENTION

The present invention is directed to antimicrobial compositions that result in a product that has superior aesthetic attributes, broad spectrum antimicrobial efficacy and is also mild to skin. More particularly, the present invention relates to antimicrobial compositions exhibiting the antimicrobial effectiveness of cationic active ingredients, a cationic compatible surfactant, a foam boosting agent, a foam structure enhancing agent and skin conditioning agent to reduced irritation to mammalian skin tissue. The composition is essentially free of aromatic biocides such as triclosan, anionic surfactants and $C_1$ to $C_4$ alcohols.

BACKGROUND OF THE INVENTION

Antimicrobial personal care compositions are known in the art. Especially useful are antimicrobial cleansing compositions, which typically are used to cleanse the skin and to kill bacteria and other microorganisms present on the skin, especially the hands, arms, and face of the user.

Antimicrobial compositions are used, for example, in the health care industry; long term care, hospitality and health/exercise facilities; food service industry, meat processing industry, and in the private sector by individual consumers. The use of antimicrobial compositions is recognized as an important factor in controlling bacteria and other microorganism populations on skin to reduce the potential spread of illnesses, particularly in healthcare and food service environments. It is important, however, that the antimicrobial compositions provide a substantial and broad spectrum reduction in microorganism populations quickly and without problems associated with toxicity or skin irritation.

In particular, antimicrobial cleansing compositions typically contain an active antimicrobial agent, an anionic surfactant for cleansing and foam generation, skin conditioning agents for cosmetic effects, dyes, perfumes, and optional thickening agents, such as clays, polymers, cellulosic derivatives, or colloids, for aesthetic effects, all in an aqueous carrier.

Several different classes of antimicrobial agents have been used in antimicrobial cleansing compositions. These include active ingredients selected from the following classes: phenolic compounds, carbanalide compounds, lower alcohols, and carboxylic acids. Each of these classes has their own unique advantages and challenges. Examples of specific antimicrobial agents include PCMX (para-chlorometa xylenol), triclosan, triclocarban, benzyl alcohol, quaternary ammonium compounds (QAC), iodine and iodine complexes and biguanides (e.g., chlorhexidine digluconate). At this time triclosan is the dominant antimicrobial active ingredient in the U.S. dermal antiseptic cleanser market.

Although there is an increasing consumer demand for products which have both an activity against bacteria and other microorganisms, there is an even greater demand to fulfill the consumer's expectations with regard to their level of concern with certain biocides such as triclocarban and triclosan.

Triclosan is disfavored as an antimicrobial agent due to environmental persistence and health concerns due to the possible formation of intermediate and/or environmental by products. Thus, a need exists for an efficacious antimicrobial personal care composition which is substantially free of biocides such as triclocarban and triclosan but that still provides adequate foam volume during wash and foam structure leading to dense, rigid and stable foam desired by consumers and is also mild to the skin. The present invention is directed to such antimicrobial compositions.

The above-mentioned disadvantages of current antimicrobial compositions are addressed by embodiments of the present invention and will be understood by reading and studying the following specification. The following summary is made by way of example and not by way of limitation. It is merely provided to aid the reader in understanding some of the aspects of the invention.

SUMMARY OF THE INVENTION

In accordance with the present invention, a composition that has superior aesthetic attributes, broad spectrum antimicrobial efficacy and is also mild to skin is provided. The antimicrobial composition comprises a cationic active ingredient, a cationic compatible surfactant which may encompass nonionic, cationic or amphoteric surfactants; a foam boosting agent, a foam structure enhancing agent, skin conditioning agents, which may include emollients, humectants, vitamins, antioxidants; and water. The present antimicrobial compositions are free of the antimicrobial agent triclosan (i.e., 2,4,4'-trichloro-2'hydroxy-diphenylether), anionic surfactants and $C_1$ to $C_4$ alcohols and have rapid cidal efficacy. The compositions also provide stable yet free-rinsing foam and may optionally contain ingredients to increase skin compatibility and skin health.

Accordingly, one aspect of the present invention is to provide an antimicrobial composition for reducing microbial population on dermal tissue, the antimicrobial composition comprising: (a) about 0.01 wt. % to about 15 wt. %, of one or more cationic actives; (b) about 0.1 wt. % to about 25 wt. %, of one or more cationic compatible surfactants (c) 0.01% to about 15% of one or more foam boosting agents (d) 0.01% to about 15% of one or more foam structure enhancing agents (e) 0.01% to about 15% of one or more skin conditioning agents, and (f) water or other suitable diluent, wherein the composition is essentially free of triclosan, anionic surfactants, cocamide DEA, betaine based surfactants, triclosan, p-chloro-m-xylenol, and iodide.

Another aspect of the present invention is to provide an antimicrobial composition for reducing microbial population on dermal tissue which is stable and has a pH of about 5.0 to about 8.0. The present composition also exhibits excellent esthetic properties, such as adequate foam volume during wash and foam structure leading to dense, rigid and stable foam. The present composition optionally contains ingredients to increase skin compatibility and health. Moreover, the composition may exhibit reduced tissue irritancy potential.

A further aspect of the present invention is to provide personal use products based on an antimicrobial composition of the present invention, for example, a skin cleanser, a surgical scrub, a hand sanitizer gel, a disinfectant, antiseptic wash, and the like.

A further aspect of the present invention is to provide a method of reducing gram positive and/or gram negative bacteria populations on mammalian tissue, including human tissue, by contacting the tissue, like the dermis, with a composition of the present invention for a sufficient time, such as about 10 seconds to 5 minutes, to reduce the bacteria level to a desired level. In some embodiments sufficient time may even be as low as 5 seconds. Antimicrobial efficacy is applicable to viral and fungal organisms as well as gram positive and gram negative bacteria.

While multiple embodiments are disclosed, still other embodiments of the present invention will become apparent to those skilled in the art from the following detailed description, which shows and describes illustrative embodiments of the invention. Accordingly, the detailed description is to be regarded as illustrative in nature and not restrictive.

DETAILED DESCRIPTION OF THE PREFERRED EMBODIMENTS

Figure 1:
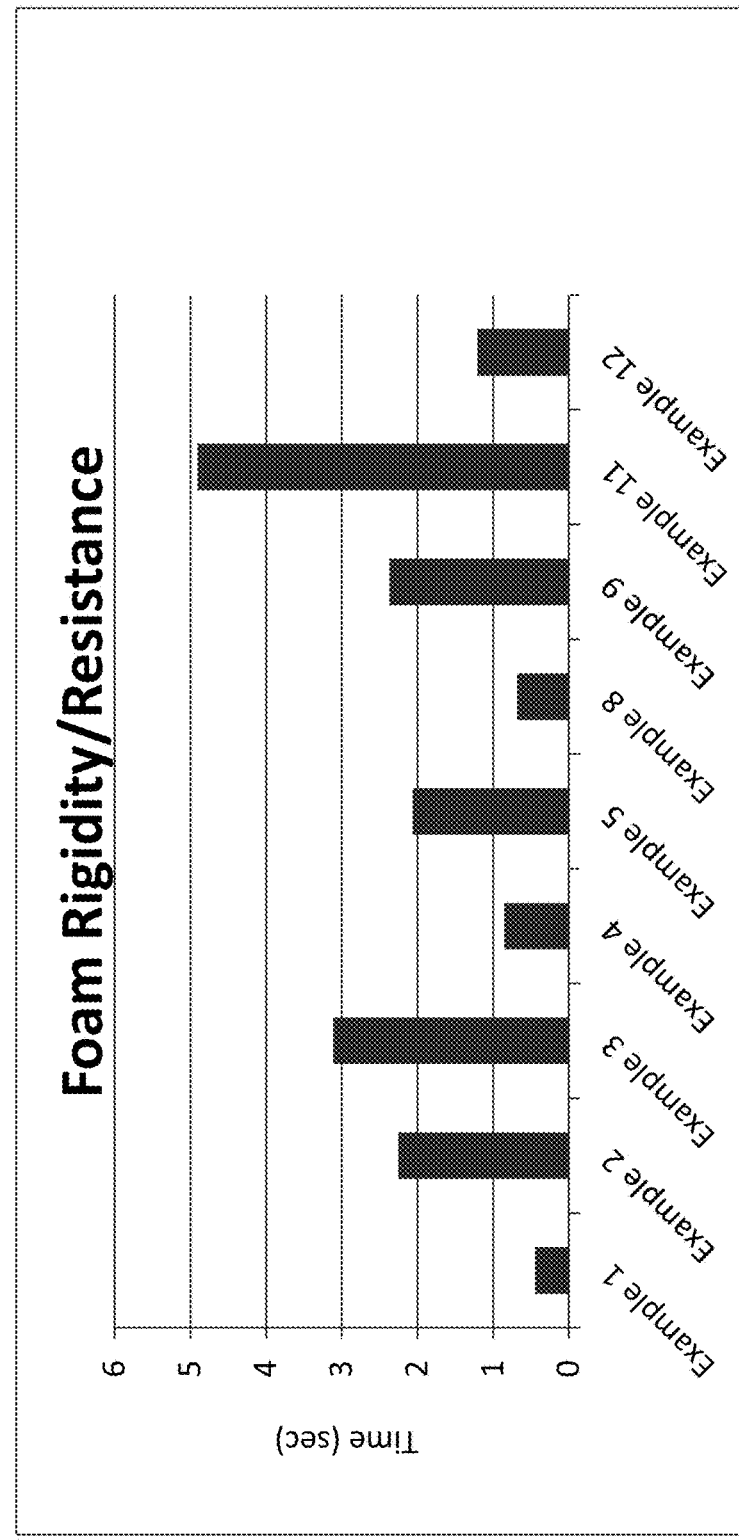
FIG. 1 is a graph showing Foam rigidity and resistance results of examples 1-5, 8, 9, 11 and 12.

Other than in the operating examples, or where otherwise indicated, all numbers expressing quantities of ingredients or reaction conditions used herein are to be understood as being modified in all instances by the term "about".

As used herein, weight percent (wt. %), percent by weight, % by weight, and the like are synonyms that refer to the concentration of a substance as the weight of that substance divided by the total weight of the composition and multiplied by 100.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities.

As used herein, the term "cationic active" is defined as the ingredient that provides antimicrobial cidal activity.

As used herein, the term "cationically compatible" means a component that does not cause an insoluble complex with the cationic active agent and/or does not substantially reduce the antimicrobial action of the cationic active agent.

As used herein, the term "skin conditioning agent" is defined as the ingredient or ingredients that improve or maintain the health of the skin and/or post wash aesthetic feel.

The term "alkyl" refers to a straight or branched chain monovalent hydrocarbon radical having a specified number of carbon atoms. As used herein, "alkyl" refers to a linear or branched $C_6$-$C_{18}$ carbon chain.

The term "microbial" or "microbial population" refers to bacterial, fungal, yeast, or viral population or combinations thereof or any mixture thereof in a laboratory or natural setting.

The term rapid cidal efficacy refers to ≥3 log kill in up to 60 seconds in the in vitro time kill test ASTM E 2315.

The term "surfactant" or "surface active agent" refers to an organic chemical that when added to a liquid changes the properties of that liquid at a surface or interface.

"Cleansing" means to perform or aid in soil removal, bleaching, microbial population reduction, rinsing, or combination thereof.

As used herein, the term "free" refers to compositions completely lacking the component or having such a small amount of the component that the component does not affect the effectiveness of the composition. The component may be present as an impurity or as a contaminant and shall be less than 0.5 wt. %. In another embodiment, the amount of the component is less than 0.1 wt. % and in yet another embodiment, the amount of component is less than 0.01 wt. %.

It should be noted that, as used in this specification and the appended claims, the singular forms "a", "an", and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The term "actives" or "percent actives" or "percent by weight actives" or "actives concentration" are used interchangeably herein and refers to the concentration of those ingredients involved in cleansing expressed as a percentage minus inert ingredients such as water or salts. Note that percentages reported in the examples section only are total percentages of components as received from commercial vendors and in those tables, do include inert ingredients such as water or salts.

As used herein, the term "substantially free" refers to compositions completely lacking the component or having such a small amount of the component that the component does not affect the performance of the composition. The component may be present as a minor constituent and/or impurity or contaminant and shall be less than 5 wt-%. In another embodiment, the amount of the component is less than 1 wt-% and in yet another embodiment, the amount of component is less than 0.1 wt-%.

As used herein, the terms "triclosan free" or "free of triclosan" refers to a composition, mixture, or ingredients that do not contain triclosan (2,4,4'-trichloro-2'hydroxy-diphenylether) or triclosan containing compounds or to which the same has not been added. Should triclosan or triclosan containing compounds be present through contamination of a composition, mixture, or ingredients, the amount of the same shall be less than 0.5 wt. %. In another embodiment, the amount of triclosan is less than 0.1 wt. % and in yet another embodiment, the amount is less than 0.01 wt. %.

Antimicrobial Compositions Containing Cationic Active Compounds

The present invention relates to an antimicrobial composition that exhibits rapid cidal antimicrobial efficacy and excellent foaming attributes. The antimicrobial composition comprises a cationic active ingredient, a cationic compatible surfactant which may encompass nonionic, amphoteric, or cationic surfactants, a foam boosting agent, a foam structure enhancing agent, a skin conditioning agent and water. The present antimicrobial compositions are free of the antimicrobial agent triclosan (i.e., 2,4,4'-trichloro-2'hydroxy-diphenylether), anionic surfactants and $C_1$ to $C_4$ alcohols, have rapid cidal efficacy and provide adequate foam volume during wash and foam structure that leads to dense, rigid and stabile foam and also contain ingredients to increase skin compatibility and skin health.

Accordingly, one aspect of the present invention is to provide an antimicrobial composition for reducing the microbial population on dermal tissue, the antimicrobial composition comprising: (a) about 0.01 wt. % to about 10 wt. %, of one or more cationic actives; (b) about 0.1 wt. % to about 12.5 wt. %, of one or more cationic compatible surfactants (c) 0.01% to about 15% of one or more foam boosting agents (d) 0.01% to about 20% of one or more foam structure enhancing agents (e) 0.01% to about 15% of one or more skin conditioning agents, and (f) water or other suitable diluent, wherein the composition is essentially free of triclosan, anionic surfactants, cocamide DEA, betaine based surfactants, triclosan, p-chloro-m-xylenol, and iodide.

Another aspect of the present invention is to provide an antimicrobial composition for reducing microbial population on dermal tissue which is stable and has a pH of about 5.0 to about 8.0. The present composition also exhibits excellent esthetic properties during the wash process, providing adequate foam volume and foam structure that leads to dense, rigid and stabile foam and ingredients to increase skin compatibility and health. Moreover, the composition may exhibit reduced tissue irritancy potential.

A further aspect of the present invention is to provide personal use products based on an antimicrobial composition of the present invention, for example, a skin cleanser, a surgical scrub, a hand sanitizer, a disinfectant, and the like.

A further aspect of the present invention is to provide a method of reducing gram positive and/or gram negative bacteria populations on mammalian tissue, including human tissue, by contacting the tissue, like the dermis, with a composition of the present invention for a sufficient time, such as about 10 seconds to 5 minutes, to reduce the bacteria level to a desired level.

The following illustrates non-limiting embodiments of the present invention.

Cationic Actives

One or more cationic actives is present in an antimicrobial composition for reducing microbial population on the dermal tissue of a mammal of the present invention in an amount of about 0.01 wt. % to about 10 wt. %, and preferably about 0.05 wt. % to about 5 wt. %, and more preferably from about 0.1 wt. % to about 4 wt. % of the composition.

The amount of antimicrobial agent in the composition is related to the end use of the composition. The amount of antimicrobial agent is sufficient in the compositions of the invention to achieve a microbial kill in a short contact time, for example, 15 to 30 seconds.

Cationic active ingredients are an antimicrobial agent useful in the present invention. The cationic active ingredients are substances based on nitrogen centered cationic moieties with net positive change. The cationic active ingredients are preferably selected from the group consisting of cationic polymers, cationic surfactants, cationic monomers, cationic silicon compounds, cationic derivatized protein hydrolyzates and betaines with at least one cationic or cationically-active group.

Suitable cationic active ingredients contain quaternary ammonium groups. Suitable cationic active ingredients especially include those of the general formula:

wherein $R^1$, $R^2$, $R^3$ and $R^4$ independently of each other represent alkyl groups, aliphatic groups, aromatic groups, alkoxy groups, polyoxyalkylene groups, alkylamido groups, hydroxyalkyl groups, aryl groups, $H^+$ ions, each with from 1 to 22 carbon atoms, with the provision that at least one of the groups $R^1$, $R^2$, $R^3$ and $R^4$ has at least eight carbon atoms and wherein X(−) represents an anion, for example, a halogen, acetate, phosphate, nitrate or alkyl sulfate, preferably a chloride. The aliphatic groups can also contain cross-linking or other groups, for example additional amino groups, in addition to the carbon and hydrogen atoms.

Particular cationic active ingredients include, for example, but are not limited to, alkyl dimethyl benzyl ammonium chloride (ADBAC, or benzalkonium chloride), alkyl dimethyl ethylbenzyl ammonium chloride, dialkyl dimethyl ammonium chloride, benzethonium chloride, N,N-bis-(3-aminopropyl)dodecylamine, chlorhexidine gluconate, a salt of chlorhexidene gluconate, PHMB (polyhexamethylene biguanide), salt of a biguanide, a substituted biguanide derivative, an organic salt of a quaternary ammonium containing compound or an inorganic salt of a quaternary ammonium containing compound or mixtures thereof.

In accordance with an important feature of the present invention, a present antimicrobial composition is substantially free of triclosan. The phrase "substantially free" of triclosan is defined as meaning that the composition contains 0% to about 0.25% by weight, in total, of triclosan. In particular, triclosan may be present in an antimicrobial composition in a total amount of 0.25% or less either as a by-product or as a component of an ingredient in the composition, but triclosan is not intentionally introduced into the composition.

Cationic Compatible Surfactant Component

The present antimicrobial composition also contains one or more cationic compatible surfactants. Such surfactants include nonionic, amphoteric or cationic surfactants. The one or more cationic compatible surfactants is present in an amount of about 0.1 wt. % to about 12.5 wt. % preferably about 0.5 wt. % to about 10 wt. %, and more preferably from about 1 wt. % to about 7.5 wt. % of the composition. In one particularly preferred embodiment, the surfactant component comprises less than 5 wt. % of the composition.

The amount of cationic compatible surfactant present in the composition is related to the amount of the cationic active in the composition, the identity of the cationic compatible surfactant, and the end use of the composition.

Suitable cationic compatible surfactants include compounds that functions as a primary cleansing and foaming ingredients, they can be (a) nonionic surfactants (b) amphoteric surfactants, or (c) cationic surfactants, or mixtures thereof. The formulation is essentially free of anionic surfactants.

Nonionic Surfactants

Examples of nonionic surfactants include, but are not limited to, amine oxide surfactants, which may be: alkyl di($C_1$-$C_7$) amine oxides in which the alkyl group has about 10-20, and preferably 12-16 carbon atoms, and can be straight or branched chain, saturated or unsaturated. Examples of such compounds include lauryl dimethyl amine oxide, myristyl dimethyl amine oxide, and those in which the alkyl group is a mixture of different amine oxide, dimethyl cocoamine oxide, dimethyl (hydrogenated tallow) amine oxide, and myristyl/palmityl dimethyl amine oxide; alkyl di(hydroxy $C_1$-$C_7$) amine oxides in which the alkyl group has about 8-20, and preferably 12-16 carbon atoms, and can be straight or branched chain, saturated or unsaturated. Examples of such compounds include bis(2-hydroxyethyl)cocoamine oxide, bis(2-hydroxyethyl) tallowamine oxide; and bis(2-hydroxyethyl)stearylamine oxide; alkylamidopropyl di($C_1$-$C_7$) amine oxides in which the alkyl group has about 8-20, and preferably 12-16 carbon atoms, and can be straight or branched chain, saturated or unsaturated. Examples of such compounds include cocoamidopropyl dimethyl amine oxide and tallowamidopropyl dimethyl amine oxide; and alkylmorpholine oxides in which the alkyl group has about 10-20, and preferably 12-16 carbon atoms, and can be straight or branched chain, saturated or unsaturated. Particularly preferred are alkyl amine oxides in which the alkyl group has about 10-14, and preferably has 12 carbon atoms, which are preferably saturated. Especially preferred is lauryl dimethyl amine oxide.

Additional nonionic surfactants include alcohol ethoxylates, fatty acid ethoxylates, alkyl phenol ethoxylate, mono-alkonaolamide ethoxylates, sorbitan esters and their ethoxylated derivatives, ethoxylated fats and oils, amine ethoxylates, ethylene oxide-propylene oxide co-polymers, glycol esters, glycerol and polyglycerol esters, sucrose esters mono and polysaccharides surfactants, such as alkyl polyglucosides.

The antimicrobial composition can contain a nonionic surfactant component that includes a detersive amount of nonionic surfactant or a mixture of nonionic surfactants. Typically, a nonionic surfactant has a hydrophobic region, such as a long chain alkyl group or an alkylated aryl group, and a hydrophilic group comprising an ethoxy and/or other hydrophilic moieties.

Amphoteric Surfactant

The cationic compatible surfactant component can include a detersive amount of amphoteric surfactant or a mixture of amphoteric surfactants. Exemplary useful amphoteric surfactants include those which may be represented by the following general formula

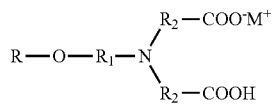

in which, R represents a $C_4$ to $C_{24}$ alkyl group, and is preferably a $C_{10}$ to $C_{16}$ alkyl group, $R_1$ and $R_2$ independently represent a $C_1$ to $C_8$ alkyl group, is preferably —$CH_2CH_2$— or —$CH_2CH_2CH_2$—, and M may be any salt-forming anion which permits water solubility or water miscibility of the compound, e.g., chloride, bromide, methosulfate, ethosulfate, lactate, saccharinate, acetate or phosphate. Such compounds are presently commercially available, such as those marketed in the Tomamine Amphoteric series of amphoteric surfactants, ex. Air Products Inc.

Additional amphoteric surfactants that can be used include, but are not limited to, imidiazolines and imidiazoline derivatives, betaine derivatives, amphoacetate derivatives, propionates, and mixtures thereof.

Exemplary betaine surfactants include those which may be represented by the general formula:

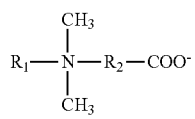

wherein $R_1$ is an alkyl group containing from 8 to 18 carbon atoms, or the amido radical which may be represented by the following general formula:

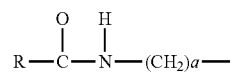

wherein R is an alkyl group having from 8 to 18 carbon atoms, a is an integer having a value of from 1 to 4 inclusive, and R2 is a C1-C4 alkylene group. Examples of such water-soluble betaine surfactants include dodecyl dimethyl betaine, as well as cocoamidopropylbetaine.

One or more amphoacetates such as sodium lauroamphoacetate, or diamphoacetates may also be used. Amphoacetates may be represented by the following general formula:

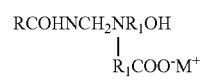

and, diamphoacetates may be represented by the following general formula:

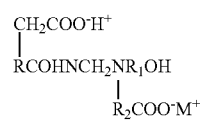

wherein in both formulas, R represents an aliphatic group having 8 to 18 carbon atoms, $R_1$ represents an aliphatic group having 1 to 5 carbon atoms, but is preferably —$CH_2$—, or —$CH_2CH_2$—, and M is a cation such as sodium, potassium, ammonium, or a substituted ammonium. Examples of such compounds include: sodium lauroamphoacetate, sodium cocoamphoacetate, disodium lauroamphoacetate, and disodium cocoamphoacetate. In a preferred embodiment the composition is substantially free of sodium cocoamphoacetate and cocoamidopropyl hydroxysultaine which may reduce the antimicrobial activity of the cationic active compound.

In a preferred embodiment the composition is also substantially free of betaine based surfactants.

Cationic Surfactant

The surfactant component of the composition may also include a detersive amount of cationic surfactant or a mixture of cationic surfactants. Cationic surfactants that can be used in the antimicrobial composition include, but are not limited to, quaternized sugar-derived surfactants, quaternized polysaccharides, quaternized alkyl polysaccharides, alkoxylated amines, alkoxylated ether amines, and mixtures thereof. The amount of cationic compatible surfactant present in the composition is related to the amount of the cationic active in the composition, to the identity of the cationic surfactant, and the end use of the composition.

The cationic compatible surfactant may be a quaternized sugar-derived surfactant that is a quaternized alkyl polyglucoside or a polyquaternized alkyl polyglucoside, and the like.

The quaternary functionalized alkyl polyglucoside is a naturally derived cationic surfactant from alkyl polyglucosides and has a sugar backbone. Quaternary functionalized alkyl polyglucosides have the following representative formula:

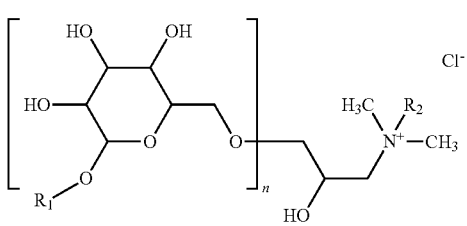

Wherein $R_1$ is an alkyl group having from about 6 to about 22 carbon atoms, and $R_2$ is $CH_3(CH_2)_{n'}$ where n' is an integer ranging from 0-21. Examples of suitable quaternary functionalized alkyl polyglucosides components which can be used in the cleansing compositions according to the present invention include those in which the $R_1$ alkyl moiety contains primarily about 10-12 carbon atoms, the $R_2$ group is $CH_3$ and n is the degree of polymerization of 1-2. Further examples of a suitable quaternary functionalized alkyl polyglucoside include, but are not limited to, the antimicrobial and antifungal quaternary functionalized alkyl polyglucosides described in U.S. Pat. Nos. 7,084,129 and 7,507,399 the disclosures of which are hereby incorporated by reference. Examples of commercially suitable quaternary functionalized alkyl polyglucosides useful in cleansing compositions of the present invention include but is not limited to: Suga®Quat TM 1212 (primarily $C_{12}$ quaternary functionalized alkyl polyglucoside), Suga®Quat L 1210 (primarily $C_{12}$ quaternary functionalized alkyl polyglucoside), and Suga®Quat S 1218 (primarily $C_{12}$ quaternary functionalized alkyl polyglucoside) available from Colonial Chemical, Inc., located in South Pittsburgh, Tenn.

A polyquaternary alkyl polyglucoside is naturally derived from alkyl polyglucosides and has a sugar backbone. Polyquaternary alkyl polyglucosides have the following representative formula:

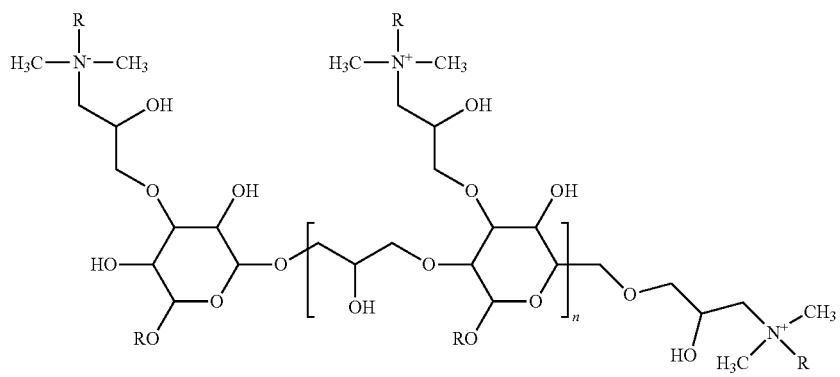

Wherein R is an alkyl group having from about 6 to about 22 carbon atoms and n is an integer ranging from 4 to 6. Examples of suitable polyquaternary functionalized alkyl polyglucosides which can be used in the compositions include those in which the R alkyl moiety contains from about 8 to about 12-carbon atoms. In a preferred embodiment the quaternary functionalized alkyl polyglucoside contains primarily about 10-12 carbon atoms. Examples of commercially suitable poly quaternary functionalized alkyl polyglucosides useful in cleansing compositions of the present invention include but is not limited to: Poly Suga®Quat series of quaternary functionalized alkyl polyglucosides, available from Colonial Chemical, Inc., located in South Pittsburgh, Tenn.

Foam Boosting Agent

The compositions of the invention include one or more foam boosting agents. These are present in the composition in an amount of from about 0.01 wt. % to about 15 wt. %, preferably from about 0.05 wt. % to about 10 wt. % and more preferably from about 1 wt. % to about 5 wt. %. Suitable foam boosting agents include compounds that increase the volume of foam in the hand of a user. Specifically, for a foaming formulation to remain in the foam phase, bubbles in the foam must maintain their shape and volume without drainage. When drainage occurs, liquid from the outer portion or skin of the bubbles drains through the foam due to gravity and the bubbles cease to exist from the top down. As the foam volume decreases, the balance of the formulation begins pooling under the remaining foam as liquid until no more bubbles exist and liquid is all that remains.

Some examples of foam boosting agents include glyceryl caprylate/caprate sorbitan sesquicaprylate, phospholipids, phospholipid derivatives, PEG dimethicone with methylesters, PEG-7 glyceryl cocoate and capric/caprylic monoglycerides.

The composition, in a preferred embodiment includes glyceryl caprylate/caprate which the inventors have identified as a foam boosting agent. The glyceryl caprylate/caprate foam boosting agent which may be present as a part of the foam boosting component, may be present in an amount of from about 0.05 wt. % to about 8 wt. %, preferably from about 0.1% to about 5 wt. %

The foam boosting component may also include a polymer. Polymers which function according to the invention comprise a hydrophobically modified cationic polymer obtainable from the polymerization of the following structural units:

(i) a first structural unit derived from one or more cationic ethylenically unsaturated monomers;

(ii) a second structural unit derived from one or more water-soluble monomers.

(i) First Structural Unit

The first structural unit is a water-soluble cationic ethylenically unsaturated monomer. The first structural unit can be a dialkyl diallyl ammonium with halides, hydrogensulfate or methosulfate as counterions according to formula (I):

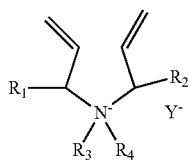

wherein:
$R_1$ and $R_2$ are, independently of one another, hydrogen or $C_1$-$C_4$ alkyl;
$R_3$ and $R_4$ are, independently of one another, hydrogen, alkyl, hydroxyalkyl, carboxyl alkyl, carboxyamide alkyl or alkoxyalkyl groups having from 1 to 18 carbon atoms; and
Y— is the counterion selected from the group consisting of chloride, bromide, iodine or hydrogensulfate or methosulfate.

In another embodiment, the first structural unit is a quaternary or acid salt of dialkyl amino alkyl(meth)acrylate. In a further embodiment, the first structural unit is an acid salt of a dialkyl amino alkyl(meth)acrylamide or a quaternary dialkyl amino alkyl(meth)acrylamide according to formula (II):

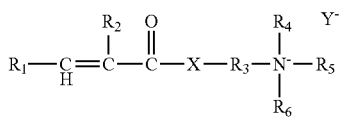

wherein;
$R_1$ is H or $C_1$-$C_4$ alkyl;
$R_2$ is H or methyl;
$R_3$ is $C_1$-$C_4$ alkylene;
$R_4$, $R_5$ and $R_6$ are each independently H or $C_1$-$C_{30}$ alkyl;
X is —O— or —NH—; and
Y is Cl; Br; I; hydrogensulfate methosulfate.

In one embodiment of the present invention, it is preferred that, in the cationic monomer of the formula (II), wherein:
$R_1$ and $R_2$ are each H or
$R_1$ is H and $R_2$ is $CH_3$ or preferably also H.
Suitable Examples of the First Structural Unit are Diallyl Dimethyl Ammonium Chloride
(DADMAC), (3-acrylamidopropyl)-trimethylammonium chloride (APTAC), (3-methacryl-amidopropyl)-trimethylammonium chloride (MAPTAC), dimethylaminopropylacrylat methochlorid, dimethylaminopropylmethacrylat methochlorid. Further suitable examples of the first structural unit are [2-(Acryloyloxy)ethyl]trimethylammonium chloride, also referred to as dimethylaminoethyl acrylate methochloride (DMA3*MeCl), or trimethyl-[2-(2-methylprop-2-enoyloxy)ethyl]azanium chloride, also referred as dimethylaminoethyl methacrylate methochloride (DMAEMA*MeCl). Preferably, the first structural unit is DADMAC.

(ii) Second Structural Unit
The Second Structural Unit is Acylamide or Methacrylamide
All wt % for each of the structural units are calculated based on 100% by weight of all structural units derived from all the monomers in the co polymer. A preferred copolymer is a DADMAC/(meth)acrylamide copolymer with a molecular weight of approximately 2,000,000 such as the Mackermium 007 line of copolymers available from Rhodia, Inc.

Foam Structure Enhancing Agent

Foam structure enhancing agents are agents that change the physical foam structure including foam stability, bubble size, density and rigidity thereby imparting sensorial attributes during the washing process. Users may describe such sensorial attributes as lather, creaminess, cushion, and/or slip.

In a preferred embodiment a novel foam structure agent is disclosed as a linear, non-substituted high molecular weight polyethylene glycol, such as PEG 300 or greater, or PEG 1000 or greater. In a particularly preferred embodiment the PEG 8000 is the foam structure enhancing agent. One or more foam structure enhancing agents are present in the in an amount of from about 0.01 wt. % to about 20 wt. %, preferably from about 0.05 wt. % to about 15 wt. % and more preferably from about 1 wt. % to about 10 wt. %.

Examples of other foam structure enhancing agents include an organic solvent, other than a short chain alcohol, typically soluble in both water and oil. Examples of foam structure enhancing agents according to the present invention include: polyols, such as glycerol (glycerin), propylene glycol, hexylene glycol, diethylene glycol, propylene glycol n-alkanols, ethylene glycol, other glycols, monooleate of ethoxylated glycerides (with 8 to 10 ethylene oxide units); esters, such as isopropyl myristate/palmitate, myristyl alcohol, lauryl alcohol, lauryl lactate, amides, such as acetamide oleates such as triolein; According to one preferred embodiment the foam stabilizer is hexylene glycol.

The foam structure enhancing agents constituent may also comprise at least one a fatty alkanolamide, examples of which include but are not limited to: cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and mixtures thereof. Alkanol amides may provide an ancillary thickening benefit as well. A preferred alkanol amide is diisopropanolamide, such as the Cola® liquid non DEA amides available from Colonial chemical which includes cocamide DIPA (diisopropanolamide), Soyamide DIPA, lauramide DIPA, or myristamide DIPA. In a preferred embodiment the composition is substantially free of DEA and/or MEA, such as in cocamide DEA.

In yet another preferred embodiment the composition includes diisopropanolamide as a part of the foam structure enhancing component. Diisopropanolamide may be present in the entire composition in an amount of from about 0.01 wt. % to about 8 wt. %, from about 0.05 wt. % to about 5 wt. % and more preferably from about 0.1 wt. % to about 3 wt. %.

Additional foam structure enhancing agents may include agents that modify slip during the hand washing process by helping the foam structure enhancing agents to flow more easily and more smoothly in the hand of a user. Examples of these agents may include; caprylyl glycol, ethylhexyl glycerine and phenoxyethanol. According to one preferred embodiment the foam structure enhancing agent is phenoxyethanol. Phenoxyethanol is often recognized as a preservative; however, it was surprisingly found that it acted as an excellent foam structure enhancing agent. The slip modifying agent is present in the composition in an amount from about 0.05 wt. % to about 10 wt. %, preferably from about 0.1 wt. % to about 7 wt. %.

Dermal Adjuvants/Skin Conditioning Agents
The composition can contain from about 0.01 wt. % to about 15 wt. % of dermal adjuvants, preferably from about 0.05 wt. % to about 10 wt. % and more preferably from about 1 wt. % to about 5 wt. %. Dermal adjuvants/skin conditioning agents generally include any substance which improves or maintains the health of the epidermis. Some examples include but are not limited to emollients, humectants, vitamins, antioxidants, skin nutrients, moisturizers and skin conditioners.

The composition can include emollients including but not limited to dicaprylyl carbonate, dibutyl adipate, hexyl laurate, dicaprylyl ether, propylheptyl caprylate. Also included are ethoxylated natural and synthetic oils. Examples include C12-15 alkyl benzoate, capric triglyceride, caprylic triglyceride, isopropyl myristrate, isopropyl palmitate, octyldodecanol, decyl oleate, cocoglycerides, ethylhexyl stearate, cetearyl isononanoate, cetearyl ethyhexanonate, decyl cocoate, cetyl dimethicone, ethylhexyl palmitate, PPG-11 stearyl ether, PPG-15 stearyl ether, and PPG-14 butyl ether.

These materials also may include derivatives of water soluble oils and waxes, ethoxylated fats and oils, lanolin ethoxylate; examples include mono-, di-, and tri-glycerides and butters and hydrogenated versions of seed and nut oils including but not limited to; palm oil, coconut oil, vegetable oil, avocado oil, canola oil, corn oil, soy bean oil, sunflower oil, safflower oil, meadowfoam seed oil, bilberry seed oil, watermelon seed oil, olive oil, cranberry, macadamia nut oil, argan oil, pomegranate oil, argan moraccan oil, blue berry oil, raspberry oil, walnut oil, pecan oil, peanut oil, bayberry oil, mango seed oil, Manila oil, castor oil, Shea butter, jojoba oil, hydrolyzed jojoba oil, Carnauba butter, Carnauba wax, castor isostearate succinate stearyl heptanoate, cetyl ricinoleate, oleyl frucate, sucrose monostearate, sucrose distearate, sucrose tristearate, sucrose tetrastearate, cetyl alcohol, lanolin, lanolin ethoxylate, low molecular weight polyethylene waxes, lower molecular weight polypropylene waxes, PEG-30 glyceryl cocoate, PEG-80 Glyceryl cocoate, PEG-30 Glyceryl stearate, PEG-8 Ricinoleate, PEG-8 Raspberriate, Linear (otherwise known as bis) and Pendant versions of including hydroxyl terminated and methyl ether terminated; PEG-3 to PEG-32 Dimethicone (including but not limited to: PEG-3 Dimethicone, PEG-8 Dimethicone, PEG-9 Dimethicone, PEG-10 Dimethicone, PEG-11 Methyl ether dimethicone, PEG-12 Dimethicone, PEG-14 Dimethicone, PEG-17 Dimethicone, PEG-32 Dimethicone), bis-PEG/PPG-20/20 Dimethicone, PEG/PPG 20/23 Dimethicone, PEG/PPG 20/22 Butyl Ether Dimethicone, PEG/PPG 23/6 Dimethicone, PEG/PPG 20/15 Dimethicone.

Alkyl modified dimethicone (stearoxy dimethicone, behenoxy dimethicone, cetyl dimethicone, certeryl methicone C30-45 Alkyl cetearyl dimethicone copolymer, C30-45 Alkyl dimethicone, caprylyl methicone, PEG-8 dimethicone/dimer dilinoleic acid copolymer, Bis-PEG-10 Dimethicone/Dimer Dilinoleate Copolymer, Stearoxymethicone/Dimethicone Copolymer, Dipheyl dimethicone, Lauryl polyglycerol-3 polydimethylsiloxyethyl dimethicone, Lauryl PEG-9 polydimethylsiloxyethyl dimethicone), Dimethicone fluid (>20 cst), quaternized ammonia silicone polymers, Amino silicones, silicone quaternium-18, Amodimethicone, phenyltrimethicone, amino silicone polyethers, Polyglycerol-3 Disiloxane dimethicone, Polyglycerol-3 polydimethylsiloxyethyl dimethicone, and PEG-9 polydimethylsiloxyethyl dimethicone.

The composition can include one or more skin conditioners such as vitamins, humectants, an occlusive agent, or other moisturizer material to provide skin moisturization, skin softening, skin barrier maintenance, anti-irritation, or other skin health benefits. Some non-limiting examples of additional skin conditioners include cationic and nonionic guar and their derivatives, alkyl benzoate, myristyl myristate, cetyl myristate, gelatin, lactic acid, glyceryl dioleate, methyl laurate, PPG-9 laurate, lauryl lacylate, allantoin, octyl palmitate, lanolin, propylene glycol, butylene glycol, ethylene glycol, caprylyl glycol, monobutyl ether, glycerine, fatty acids, proline, natural oils such as almond, mineral, canola, sesame, soybean, pyrrolidine, wheat germ, hydrolyzed wheat protein, hydrolyzed oat protein, hydrolyzed collagen, corn, peanut and olive oil, isopropyl myristate, myristyl alcohol, aloe vera, algae extract, cocamidopropyl PG dimmonium chloride phosphate, gluconic acid, hydrolyzed silk protein, 1,3-propane-diol, Vitamin E, nicatinamide, stearyl alcohol, isopropyl palmitate, sorbitol, amino acid complexes, panthenol, Cocoamidopropyl PG Dimonium Chloride, quaternized hydrolyzed protein such as collagen, oat, wheat, etc. . . . , inositol, fructose, sucrose, hydrolyzed plant proteins, seaweed extract, polyethylene glycol, ammonium lactate, sodium hyaluronate, and cyclic peptides.

Some non-limiting examples of humectants include hydroxyethyl urea, agarose, urea, fructose, glucose, glutamic acid, glycerine, honey, lactose, maltose, polyethylene glycol, sorbitol and mixtures thereof.

Some non-limiting examples of occlusive agents include ethoxylated petrolatum, ethoxylated version of shea butter, avocado oil, balm mint oil, cod liver oil, mineral oil, trimyristin, stearyl stearate, synthetic wax, or mixtures thereof. Some non-limiting examples of other moisturizers include ethyl hexylglycerin, cholesterol, cystine, hyaluronic acid, keratin, lecithin, egg yolk, glycine, PPG-12, polyquaternium polymers such as polyquaternium-11, behentrimonium chloride, dihydroxypropyl PEG-5 linoleammonium chloride, glycerol oleate, PEG-7 glyceryl cocoate, cocoglucoside, PEG-200 hydrogenated glyceryl palmate, panthenol, retinol, salicylic acid, vegetable oil, methyl gluceth-10, methyl gluceth-20, ethoxylated derivatives of skin conditioners such as glycereth-26 and ethoxylated shea butter, and mixtures thereof. Finally, some non-limiting examples of anti-irritants include bisabolol and panthenol.

The skin conditioner may include an antioxidant for improved skin condition through the removal of free radicals, and improved product stability. Some non-limiting examples of antioxidants include retinol and retinol derivatives, ascorbic acid and ascorbic acid derivatives, BHA, BHT, beta carotene, cysteine, erythorbic acid, hydroquinone, tocopherol and tocopherol derivatives, and the like.

Preservatives

The composition may optionally include a preservative. Generally, preservatives fall into specific classes including phenolics, halogen compounds, quaternary ammonium compounds, metal derivatives, amines, alkanolamines, nitro derivatives, biguanides, analides, organosulfur and sulfur-nitrogen compounds, alkyl parabens, and miscellaneous compounds. Some non-limiting examples of phenolic preservative agents include pentachlorophenol, orthophenylphenol, chloroxylenol, p-chloro-m-cresol, p-chlorophenol, chlorothymol, m-cresol, o-cresol, p-cresol, isopropyl cresols, mixed cresols, phenoxyethanol, phenoxyethylparaben, phenoxyisopropanol, phenyl paraben, resorcinol, and derivatives thereof. Some non-limiting examples of halogen compounds include sodium trichloroisocyanurate, sodium dichloroisocyanurate, iodine-poly(vinylpyrolidinonen) complexes, and bromine compounds such as 2-bromo-2-nitropropane-1,3-diol, and derivatives thereof. Some non-limiting examples of quaternary ammonium compounds include benzalkonium chloride, benzethonium chloride, behentrimonium chloride, cetrimonium chloride, and derivatives thereof. Some non-limiting examples of amines and nitro containing compounds include hexahydro-1,3,5-tris(2-hydroxyethyl)-s-triazine, dithiocarbamates such as sodium dimethyldithiocarbamate, and derivatives thereof. Some non-limiting examples of biguanides include polyaminopropyl biguanide and chlorhexidine gluconate. Some non-limiting examples of alkyl parabens include methyl, ethyl, propyl and butyl parabens.

The preservative is preferably present in the composition in an amount from about 0.01 wt. % to about 5 wt. %, from about 0.05 wt. % to about 3 wt. %, and from about 0.1 wt. % to about 2 wt. %.

Carrier

The carrier of the present antimicrobial composition comprises water, propylene glycol, glycerols, alcohols or mixtures thereof. It should be appreciated that the water may be provided as deionized water or as softened water. The water provided as part of the composition can be relatively free of hardness. It is expected that the water can be deionized to remove a portion of the dissolved solids. That is, the concentrate can be formulated with water that includes dissolved solids, and can be formulated with water that can be characterized as hard water. The carrier present in the composition can be present in an amount of from about 30 wt. % to about 99 wt. %, preferably from about 55 wt. % to about 97 wt. % and more preferably from about 68 wt. % to about 95 wt. %.

Optional pH Adjusting Agent

The antimicrobial composition of the present invention does not rely upon a low pH or a high pH to provide a rapid reduction in microbial populations. The composition for the present invention has a pH of about 5.0 to about 8.0. Within this pH range, the present composition effectively reduces microbial populations, and is consumer acceptable, i.e., provides adequate foam volume during wash generates stable, dense and rigid foam and is mild to skin and phase stable.

In some instances a pH adjusting compound may be necessary in a sufficient amount to provide a desired composition pH. To achieve the full advantage of the present invention, the pH-adjusting compound is present in an amount of about 0.05% to about 3.5%, by weight.

Examples of basic pH-adjusting compounds include, but are not limited to, ammonia; mono-, di-, and trialkyl amines; mono-, di-, and trialkanolamines; alkali metal and alkaline earth metal hydroxides; alkali metal phosphates; alkali sulfates; alkali metal carbonates; and mixtures thereof. However, the identity of the basic pH adjuster is not limited, and any basic pH-adjusting compound known in the art can be used. Specific, nonlimiting examples of basic pH-adjusting compounds are ammonia; sodium, potassium, and lithium hydroxide; sodium and potassium phosphates, including hydrogen and dihydrogen phosphates; sodium and potassium carbonate and bicarbonate; sodium and potassium sulfate and bisulfate; monoethanolamine; trimethylamine; isopropanolamine; diethanolamine; and triethanolamine.

The identity of an acidic pH-adjusting compound is not limited and any acidic pH-adjusting compound known in the art, alone or in combination, can be used. Examples of specific acidic pH-adjusting compounds are the mineral acids and polycarboxylic acids. Nonlimiting examples of mineral acids are hydrochloric acid, nitric acid, phosphoric acid, and sulfuric acid. Nonlimiting examples of polycarboxylic acids are citric acid, glycolic acid, and lactic acid.

Additional Functional Materials

The antimicrobial composition can include additional components or agents, such as additional functional materials. As such, in some embodiments, the antimicrobial composition comprises a cationic active ingredient, a cationic compatible surfactant, a foam boosting agent, foam structure enhancing agent, skin conditioning agent and water or even all of the total weight of the antimicrobial composition, for example, in embodiments having few or no additional functional materials disposed therein. The functional materials provide desired properties and functionalities to the antimicrobial composition. For the purpose of this application, the term "functional materials" include a material that when dispersed or dissolved in a use and/or concentrate solution, such as an aqueous solution, provides a beneficial property in a particular use. The antimicrobial composition comprises a cationic active ingredient, a cationic compatible surfactant, a foam boosting agent, a foam structure enhancing agent, skin conditioning agent and water. It may optionally contain chelants, pH adjusting compound, antioxidants, fragrances, dyes, other disinfectants, sanitizers, thickening or gelling agents, or mixtures thereof. Some particular examples of functional materials are discussed in more detail below, but it should be understood by those of skill in the art and others that the particular materials discussed are given by way of example only, and that a broad variety of other functional materials may be used. For example, many of the functional materials discussed below relate to materials used in disinfecting and/or cleansing applications, but it should be understood that other embodiments may include functional materials for use in other applications.

Chelating Agent

The composition is generally a concentrate or a ready to use composition that can optionally include a chelating agent. In general, a chelating agent is a molecule capable of coordinating (i.e., binding) the metal ions commonly found in water sources to prevent the metal ions from interfering with the action of the other ingredients. Examples of chelating agents include phosphonic acid and phosphonates, phosphates, aminocarboxylates and their derivatives, pyrophosphates, ethylenediamine and ethylenetriamine derivatives, hydroxyacids, and mono-, di-, and tri-carboxylates and their corresponding acids. In certain embodiments the composition is phosphate free. Preferred chelating agents form calcium-chelating agent complexes with a stability constant (expressed in logarithmic form) of about 5.5 or greater. The calcium-chelating agent stability constant (K) is the measure of the stability of a calcium-chelating agent complex (CaL) formed by the reaction of a calcium ion (Ca) with a chelating agent (L) in aqueous solution.

The stability constant is expressed as:

$$K = \frac{[CaL]}{[Ca][L]}$$

Where:
K=stability constant for the calcium-chelating agent complex
[CaL]=concentration (mol/L) of the calcium-chelating agent complex
[Ca]=concentration (mol/L) of calcium ions
[L]=concentration (mol/L) of the chelating agent Preferred chelating agents are selected from the group comprising ethylenediaminetetraacetic acid (EDTA); diethylenetriaminepentacetic acid (DTPA); methylglycine-N,N-diacetic acid (MGDA); glutamic acid-N,N-diacetic acid (GLDA); Aspartic acid-N,N-diacetic acid (ASDA) and alkali, alkali earth metal, transition metal and/or ammonium salts thereof.

Thickener

The composition may optionally include a thickener. Exemplary thickeners include (1) cellulosic thickeners and their derivatives, (2) natural gums, (3) starches, (4) stearates, and (5) fatty acid alcohols. Some non-limiting examples of cellulosic thickeners include carboxymethyl hydroxyethylcellulose, cellulose, hydroxybutyl methylcellulose, hydroxyethylcellulose, hydroxypropylcellulose, hydroxypropyl methyl cellulose, methylcellulose, microcrystalline cellulose, sodium cellulose sulfate, and the like. Some non-limiting examples of natural gums include acacia, calcium carrageenan, guar, gelatin, guar gum, hydroxypropyl guar, karaya gum, kelp, locust bean gum, pectin, sodium carrageenan, tragacanth gum, xanthan gum, and the like. Some non-limiting examples of starches include oat flour, potato starch, wheat flour, wheat starch, and the like. Some non-limiting examples of stearates include PEG-150 distearate, methoxy PEG-22/dodecyl glycol copolymer, and the like. Some non-limiting examples of fatty acid alcohols include caprylic alcohol, cetearyl alcohol, lauryl alcohol, oleyl alcohol, palm kernel alcohol, and the like.

The amount of thickener in the composition depends on the desired viscosity of the composition.

Fragrance

The composition may optionally include a fragrance. Examples of possible fragrances include, but are not limited to natural oils or naturally derived materials, and synthetic fragrances such as hydrocarbons, alcohols, aldehydes, ketones, esters, lactones, ethers, nitriles, and polyfunctionals. Non-limiting examples of natural oils include the following: basil (*Ocimum basilicum*) oil, bay (*Pimento acris*) oil, bee balm (*Monarda didyma*) oil, bergamot (*Citrus aurantium bergamia*) oil, cardamom (*Elettaria cardamomum*) oil, cedarwood (*Cedrus atlantica*) oil, chamomile (*Anthemis nobilis*) oil, cinnamon (*Cinnamomum cassia*) oil, citronella (*Cymbopogon nardus*) oil, clary (*Salvia sclarea*) oil, clove (*Eugenia caryophyllus*) oil, cloveleaf (*Eufenia caryophyllus*) oil, *Cyperus esculentus* oil, cypress (*Cupressus sempervirens*) oil, *Eucalyptus citriodora* oil, geranium maculatum oil, ginger (*Zingiber officinale*) oil, grapefruit (*Citrus grandis*) oil, hazel (*Corylus avellana*) nut oil, jasmine (*Jasminum officinale*) oil, *Juniperus communis* oil, *Juniperus oxycedrus* tar, *Juniperus virginiana* oil, kiwi (*Actinidia chinensis*) water, lavandin (*Lavandula hybrida*) oil, lavender (*Lavandula angustifolia*) oil, lavender (*Lavandula angustifolia*) water, lemon (*Citrus medica limonum*) oil, lemongrass (*Cymbopogon schoenanthus*) oil, lime (*Citrus aurantifolia*) oil, linden (*Tilia cordata*) oil, linden (*Tilia cordata*) water, mandarin orange (*Citrus nobilis*) oil, nutmeg (*Myristica fragrans*) oil, orange (*Citrus aurantium dulcis*) flower oil, orange (*Citrus aurantium dulcis*) oil, orange (*Citrus aurantium dulcis*) water, patchouli (*Pogostemon cablin*) oil, peppermint (*Menthe piperita*) oil, peppermint (*Menthe peperita*) water, rosemary (*Rosmarinus officinalis*) oil, rose oil, rose (*Rosa damascena*) extract, rose (*Rosa multiflora*) extract, rosewood (*Aniba rosaeodora*) extract, sage (*Salvia officinalis*) oil, sandalwood (*Santalum album*) oil, spearmint (*Menthe viridis*) oil, tea tree (*Melaleuca alternifolia*) oil, and ylang ylang (*Cananga odorata*) oil. Some non-limiting examples of synthetic hydrocarbon fragrances include caryophyllene, β-farnesene, limonene, α-pinene, and β-pinene. Some non-limiting examples of synthetic alcohol fragrances include bacdanol, citronellol, linalool, phenethyl alcohol, and α-terpineol (R=H). Some non-limiting examples of synthetic aldehyde fragrances include 2-methyl undecanal, citral, hexyl cinnamic aldehyde, isocycolcitral, lilial, and 10-undecenal. Some non-limiting examples of synthetic ketone fragrances include cashmeran, α-ionone, isocyclemone E, koavone, muscone, and tonalide. Some non-limiting examples of synthetic ester fragrances include benzyl acetate, 4-t-butylcyclohexyl acetate (cis and trans), cedryl acetate, cyclacet, isobornyl acetate, and α-terpinyl acetate (R=acetyl). Some non-limiting examples of synthetic lactone fragrances include coumarin, jasmine lactone, muskalactone, and peach aldehyde. Some non-limiting examples of synthetic ether fragrances include ambroxan, anther, and galaxolide. Some non-limiting examples of synthetic nitrile fragrances include cinnamonitrile and gernonitrile. Finally, some non-limiting examples of synthetic polyfunctional fragrances include amyl salicylate, isoeugenol, hedione, heliotropine, lyral, and vanillin.

The composition may include a mixture of fragrances including a mixture of natural and synthetic fragrances. The fragrance can be present in a composition in an amount up to about 5 wt. %, preferably from 0 to about 3 wt. %, from about 0 to about 1 wt. %, and from about 0 to about 0.2 wt. %.

Dye

The composition may optionally include a dye. Examples of dyes include any water soluble or product soluble dye, any FD&C or D&C approved dye.

Methods of Making the Compositions

The compositions of to the invention are easily produced by any of a number of known art techniques. Conveniently, a part of the water is supplied to a suitable mixing vessel further provided with a stirrer or agitator, and while stirring, the remaining constituents are added to the mixing vessel, including any final amount of water needed to provide to 100% wt. of the inventive composition.

The compositions may be packaged in any suitable container particularly flasks or bottles, including squeeze-type or pump bottles, as well as bottles provided with a spray apparatus (e.g. trigger spray) which is used to dispense the composition by spraying. The selected packaging may have a pump head foamer. Examples of commercially available pump head foamers include the F2 foamer from Rexam PLC (London, England, formerly Airspray), and the RF-17 Palm Foamer from Rieke Corporation (Auburn, Ind.). Accordingly the compositions are desirably provided as concentrates or ready to use products in manual or automated dispensing equipment.

The composition may be provided in various packaging sizes. Examples of packaging sizes include 1.5 oz, 500 ml and 1 liter bottles.

Whereas the compositions of the present invention are intended to be used in the types of liquid forms described, nothing in this specification shall be understood as to limit the use of the composition according to the invention with a further amount of water to form a solution there from. Conversely, nothing in the specification shall be also understood to limit the forming of a "super-concentrated" composition based upon the composition described above Such a super-concentrated ingredient composition is essentially the same as the compositions described above except in that they include a lesser amount of water.

Methods Employing the Compositions

The invention includes compositions and methods for reducing the population of microorganisms on skin, a method for treating a disease of skin, and the like. These compositions and methods can operate by contacting the body with a composition of the invention. Contacting can include any of numerous methods for applying a composition of the invention, such as spraying the compositions, immersing, foam or gel treating the skin with the composition, or a combination thereof. The compositions and methods may be used without further dilution with water or other suitable diluents or may be supplied as concentrated compositions The compositions of the invention can be included in any skin application products such as, sanitizers, deodorizers, antiseptics, fungicides, germicides, virucides, waterless hand sanitizers, and pre- or post-surgical scrubs, preoperative skin preps.

Embodiments of the Present Invention

The antimicrobial composition of the present invention has a high broad spectrum of antimicrobial efficacy, adequate foam volume during wash and foam structure leading to dense, rigid, and stable foam desired by consume and low irritation to mammalian tissue. Exemplary compositions are provided in the following table.

a function of time. In this test, a diluted aliquot of the composition is brought into contact with a known population of test bacteria for a specified time period at a specified temperature. The test composition is neutralized at the end of the time period, which arrests the antimicrobial activity of the composition. The percent or, alternatively, log reduction from the original bacteria population is calculated. In general, the time kill method is known to those skilled in the art. In addition, comparative data on the foam profile of representative systems is shown.

(b) The composition can be tested at any concentration from 0-100%. The choice of which concentration to use is at the discretion of the investigator, and suitable concentrations are readily determined by those skilled in the art. All testing if performed in triplicate, the results are combined, and the average log reduction is reported.

(c) The choice of contact time period also is at the discretion of the investigator. Any contact time period can be chosen. Typical contact times range from 10 second to 5 minutes, with 30 seconds and 1 minute being typical contact times. The contact temperature also can be any temperature, typically room temperature, or about 25 degrees Celsius.

TABLE A

Antimicrobial Composition with improved Foam Profile (Expressed as Weight Percentage of Actives) (pH 5.0-6.7)

| Ingredient | Example | preferred | | More preferred | | Most preferred | |
|---|---|---|---|---|---|---|---|
| Cationic Active Ingredient | Quaternary Ammonium Compound (QAC) [Alkyl Dimethyl Benzyl Ammonium Chloride (ADBAC)] | 0.01 | 10 | 0.05 | 5 | 0.1 | 4 |
| Compatible Surfactant | Lauryl Dimethyl amine oxide | 0.1 | 12.5 | 0.5 | 10 | 1 | 7.5 |
| Foam Booster | Glyceryl Caprate/Caprate Cocamidopropyl PG Dimonium Chloride Phosphate | 0.01 | 15 | 0.05 | 10 | 1 | 5 |
| Foam Structure Enhancing Agent | PEG 8000, Hexylene Glycol Disopropoponal amide. Phenoxyethanol | 0.01 | 20 | 0.05 | 15 | 1 | 10 |
| Dermal Adjuvants | PEG 12 dimethicone, Vitamin E, glycerine, methyl glueth-20, hydroxypropyl guar hydroxypropytrimonium chloride | 0.01 | 15 | 0.05 | 10 | 1 | 5 |
| Carrier | Deionized water | 30 | 99 | 55 | 97 | 68 | 95 |

EXAMPLES

The present invention is more particularly described in the following examples that are intended as illustrations only, since numerous modifications and variations within the scope of the present invention will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques.

The following methods were used in the preparation and testing of the examples:
Antimicrobial and Microbial Efficacy:
(a) Determination of Time Kill Activity:

The activity of antimicrobial compositions was measured by the time kill method [ASTM E 2315 *Standard Guide for Assessment of Antimicrobial Activity Using a Time Kill Procedure*], whereby the survival of challenged organisms exposed to an antimicrobial test composition is deterred as (d) The microbial suspension, or test inoculum, is prepared by growing a microbial culture on any appropriate solid media (e.g., agar). The microbial population then is washed from the agar with sterile physiological saline and the population of the microbial suspension is adjusted to about $10^8$ colony forming units per ml (cfu/ml).

(e) The table below lists the test microbial cultures used in the following tests and includes the name of the bacteria, the ATCC (American Type Culture Collection) identification number, and the abbreviation for the name of the organism used hereafter.

| Organism Name | ATCC # | Abbreviation |
|---|---|---|
| *S. aureus* | 6538 | *S. aureus* |
| *Escherichia coli* | 112229 | *E. coli* |

*S. aureus* is a Gram positive bacteria, whereas, *E. coli* is a Gram negative bacteria.

The log reduction is calculated using the formula:

Log reduction=$\log_{10}$(numbers control)–$\log_{10}$(test sample survivors).

Foam Height Determination

The foam height was determined with the following procedural steps:

1. Prepare a 1% solution of the product in 5 grain water.

2. Pour 150 mL of the solution into a blender

3. Mix on medium speed 10 seconds.

4. Pour into a 1000 mL beaker and measure foam height.

5. Measure foam height at 3 and 5 minutes.

Foam Resistance Determination

The foam resistance was determined by measuring 40 grams of the test product into a blender and blending for about 30 seconds on medium speed. Thereafter, the test solution was poured into a cylinder and a plastic ball was dropped into the test solution and timed to determine how many seconds it took for the plastic ball to drop from a first pre-determined level to a second pre-determined level, e.g., from 100 mL mark on the cylinder to the 40 mL mark on the cylinder.

The following table reports various formulations made and tested. Note that percentages reported in this section only are total percentages of components as received from commercial vendors and in these tables, do include inert ingredients such as water or salts. In each instance where this occurs, the percentage of active component in the product as received from the vendor is listed and percent actives can easily be calculated from this information.

Formulation Examples 1-12, 17-18

TABLE # 1

| Example formulations 1-12, 17-18 | | | | | | | | | | | | | | |
|---|---|---|---|---|---|---|---|---|---|---|---|---|---|---|
| Raw Material | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 | Ex. 17 | Ex. 18 |
| Water | 86.20 | 84.70 | 79.70 | 85.85 | 84.35 | 85.60 | 80.50 | 85.95 | 84.45 | 84.10 | 79.10 | 85.80 | 85.70 | 91.20 |
| Lauryl Dimethyl Amine Oxide (30%) | 12.50 | 12.50 | 12.50 | 12.50 | 12.50 | 12.50 | 12.50 | 12.50 | 12.50 | 12.50 | 12.50 | 12.50 | 12.50 | |
| Benzalkonium Chloride (50%) | 1.30 | 1.30 | 1.30 | 1.30 | 1.30 | 1.30 | 1.30 | 1.30 | 1.30 | 1.30 | 1.30 | 1.30 | 1.30 | 1.30 |
| Polyethylene Glycol 8000 | | 1.50 | 1.50 | | 1.50 | | | | 1.50 | 1.50 | 1.50 | | | 1.50 |
| Hexylene Glycol | | | 5.00 | | | | 5.00 | | | | 5.00 | | | 5.00 |
| Myrstamide Diisopropanolamide | | | | 0.35 | 0.35 | 0.35 | 0.35 | | | 0.35 | 0.35 | | | 0.35 |
| Glyceryl Caprylate/Caprate | | | | | | 0.25 | 0.35 | 0.25 | 0.25 | 0.25 | 0.25 | | | 0.25 |
| Phenoxyethanol | | | | | | | | | | | | 0.40 | | 0.40 |
| Dialkyldimethylammonium chloride acrylamide copolymer (10%) | | | | | | | | | | | | | 0.50 | |
| Total | 100.00 | 100.00 | 100.00 | 100.00 | 100.00 | 100.00 | 100.00 | 100.00 | 100.00 | 100.00 | 100.00 | 100.00 | 100.00 | 100.00 |

Efficacy Test Results

TABLE 2

Antimicrobial Efficacy results of examples 1-3

| Formulation | S. aureus (ATCC # 6538) | E. coli (ATCC # 112229) | Exposure Time |
|---|---|---|---|
| Example 1 | >5.39 | >5.73 | 30 seconds |
| Example 2 | >5.39 | >5.73 | 30 seconds |
| Example 3 | >5.39 | >5.73 | 30 seconds |
| Example 4 | >5.39 | >5.73 | 30 seconds |

The efficacy testing results in Table 2 demonstrates that introducing foam structure enhancing agents like PEG 8000, Hexylene Glycol, and Myristamide diisoamidopropyl amide or a combination of them does not interfere with the antimicrobial efficacy of cationic active, Benzalkonium Chloride.

Foam Height Test Results of Examples 1-11

The foam heights of the formulations were determined by preparing 1% solution and using a rotational device. The device was rotated for 2 minutes and the foam height was recorded after 30 seconds, 3 and 5 minutes.

TABLE # 3

Foam height result for examples 1-11, 17-18

| | Foam Height l(ml) | | | | | | | | | | | | |
|---|---|---|---|---|---|---|---|---|---|---|---|---|---|
| | Example 1 | Example 2 | Example 3 | Example 4 | Example 5 | Example 6 | Example 7 | Example 8 | Example 9 | Example 10 | Example 11 | Example 17 | Example 18 |
| 30 sec | 124 | 134 | 144 | 132 | 132 | 156 | 160 | 150 | 150 | 156 | 166 | 128 | 118 |
| 3 min | 124 | 132 | 134 | 122 | 130 | 144 | 158 | 144 | 144 | 144 | 158 | 124 | 114 |
| 5 min | 116 | 132 | 134 | 120 | 126 | 144 | 158 | 138 | 140 | 144 | 156 | 120 | 110 |

As shown on table 3, formulation example 7 has significantly higher foam height which was contributed by foam boosting agent, Glyceryl Caprylate/Caprate. Therefore, Glyceryl Caprylate/Caprate is a primary foam boosting agent in the preferred formula. Also shown on table 3, formulation example 11 exhibits greater foam height, this is due to combining foam boosting and foam structure enhancing components like; Glyceryl Caprylate, Polyethylene 8000, Hexylene Glycol, and Myristamide Diisopropanolamide, the optimal foam height can be achieved. Also shown on table 3, formulation example 18, it is critical to have a cationic compatible surfactant for foam generation.

Results Foam Resistance Determination

The foam resistance was determined by measuring 40 mls of the test product into a blender and blending for about 30 seconds on medium speed. The test solution was poured into a graduated cylinder and a plastic ball was dropped into the test solution and timed to determine how many seconds it took for the plastic ball to drop from 100 mL mark on the cylinder to the 40 mL mark.

FIG. 1: Foam Rigidity and Resistance Results of Examples 1-5, 8, 9, 11 and 12

As shown on FIG. 1, formulation example 2 has the most rigid foam when compare to formulation examples 1, 4, 8 and 12. Therefore, Polyethylene Glycol 8000 is a primary contributor for foam rigidity and resistance. Also shown in FIG. 1 with formulation example 3 the combination of Polyethylene Glycol and Hexylene Glycol is essential for foam rigidity and resistance. Optimal foam rigidity and resistance can be achieved when combining foam boosting agent like Glyceryl Caprylate/Caprate and foam structure enhancing components like, Polyethylene 8000, Hexylene Glycol, and Myristamide Diisopropanolamide,

| Example 13 | | |
|---|---|---|
| Description | Purpose | Wt % |
| USP Purified Water | Diluent | 80.59 |
| Benzalkonium Chloride, 50% | Active | 1.06 |
| Lauryl Dimethylamine Oxide, 30% | Compatible Surfactant | 13.00 |
| Alkyl Polyglycoside, 50% | Foam Booster | 0.60 |
| Polyquaternium-77, 28% | Foam Booster | 1.80 |
| Glycerine | Skin | 1.00 |
| PEG-7 Glyceryl Cocoate | Conditioning | 1.00 |
| Glycereth-18 ethylhexanoate (and) glycereth-18 | Agents | 0.25 |
| Polyquaternium-10 | | 0.20 |
| Chloro-2-methyl-4-isothiazolin-3-one and 2-methyl-4-isothiazolin-3-one | Preservative | 0.10 |
| Citric Acid, 50% | pH adjuster | 0.40 |
| Total | | 100.00 |

| Example 14 | | |
|---|---|---|
| Description | Purpose | Wt % |
| USP Purified Water | Diluent | 80.89 |
| Benzalkonium Chloride, 50% | Active | 1.30 |
| Lauryl Dimethylamine Oxide, 30% | Cationic | 11.00 |
| Soyamidopropyldimethylamine Oxide, 30% | Compatible Surfactant | 1.50 |
| Sorbitan Sesquicaprylate | Foam Booster | 0.30 |
| Cocamidopropyl PG Dimonium Chloride Phosphate, 47% | | 1.65 |
| Hydroxypropyl Guar Hydroxypropyltrimonium chloride | Skin Conditioning | 0.20 |
| Vitamine E Acetate | Agents | 0.08 |
| Glycerine | | 1.50 |
| Lauryl Methyl Gluceth-10 Hydroxypropyldimonium Chloride | | 0.50 |
| PEG 7 Glyceryl Cocoate | | 0.35 |
| PEG-12 Dimethicone | | 0.15 |
| Chloro-2-methyl-4-isothiazolin-3-one and 2-methyl-4-isothiazolin-3-one | Preservative | 0.10 |
| Citric Acid 50% | pH adjuster | 0.40 |
| Potassium Hydroxide, 45% | | 0.05 |
| Fragrance | Fragrance | 0.03 |
| Total | | 100.00 |

Example 15

| Description | Purpose | wt % |
|---|---|---|
| USP Purified Water | Diluent | 73.80 |
| Benzalkonium Chloride, 50% | Active | 1.30 |
| Lauryl Dimethylamine Oxide, 30% | Cationic Compatible Surfactant | 12.50 |
| Glyceryl Caprylate/Caprate | Foam Booster | 0.25 |
| Cocamidopropyl PG Dimonium Chloride Phosphate, 47% | | 2.00 |
| Polyethylene Glycol 8000 | Foam Structure Supporter | 1.50 |
| Hexylene Glycol | | 5.00 |
| Myristamide Diisopropanolamide | | 0.35 |
| Phenoxyethanol | | 0.40 |
| Hydroxypropyl Guar | Skin Conditioning Agents | 0.20 |
| Hydroxypropyltrimonium chloride | | |
| Vitamine E Acetate | | 0.10 |
| Glycerine | | 1.50 |
| Methyl Glueth-20 | | 0.50 |
| PEG-12 Dimethicone | | 0.15 |
| Citric Acid 50% | pH adjuster | 0.37 |
| Potassium Hydroxide 45% | | 0.05 |
| Fragrance | Fragrance | 0.03 |
| Total | | 100.00 |

Examples 13-15 are all Based on Cationic Active Formulas

Efficacy Results of Examples 13-15

TABLE 4

Antimicrobial efficacy result of examples 13-15

| Formulation | pH | S. aureus | E. coli | Exposure Time |
|---|---|---|---|---|
| Example 13 | 6.25 | >5.39 | >5.78 | 30 seconds |
| Example 14 | 6.25 | >5.39 | >5.78 | 30 seconds |
| Example 15 | 6.25 | >5.84 | >5.74 | 15 seconds |
| Example 15 | 6.25 | >5.39 | >5.78 | 30 seconds |

Example formulation 13, 14 and 15 are various formulations based on cationic active. Example formulation 15 contains unique foam boosting and foam structure enhancing agents. The addition of these novel agents improves the product aesthetic profile thereby improving product acceptability by consumers without disrupting the antimicrobial effectiveness of cationic active. As seen on Table 4, all formulations maintained high cidal antimicrobial efficacy. The 15 second test of Example 15 was performed on a different day than the 30 second tests. Thus, there were likely differences in bacteria populations, which may contribute to the differences in log reduction between the 30 second test and 15 second test data.

Foam Height Test Results of Examples 13-15

TABLE 5

Foam height measurements of examples 13-15

| Foam Height (ml) | Example 13 | Example 14 | Example 15 |
|---|---|---|---|
| 30 sec | 134 | 141 | 176 |
| 3 min | 128 | 130 | 168 |
| 5 min | 122 | 120 | 166 |

Example 15 has significantly higher foam height at 30 sec, 3 and 5 minutes compare to formulation example 13 and 14. This demonstrates that the addition of foam boosting and foam structure enhancing agents Glyceryl Caprylate/Caprate, PEG 8000 and Hexylene Glycol Myristamide Diisopranolamide to the cleaning composition increases foam height thereby increasing consumer product preference.

Results Foam Resistance Determination

Figure 2:
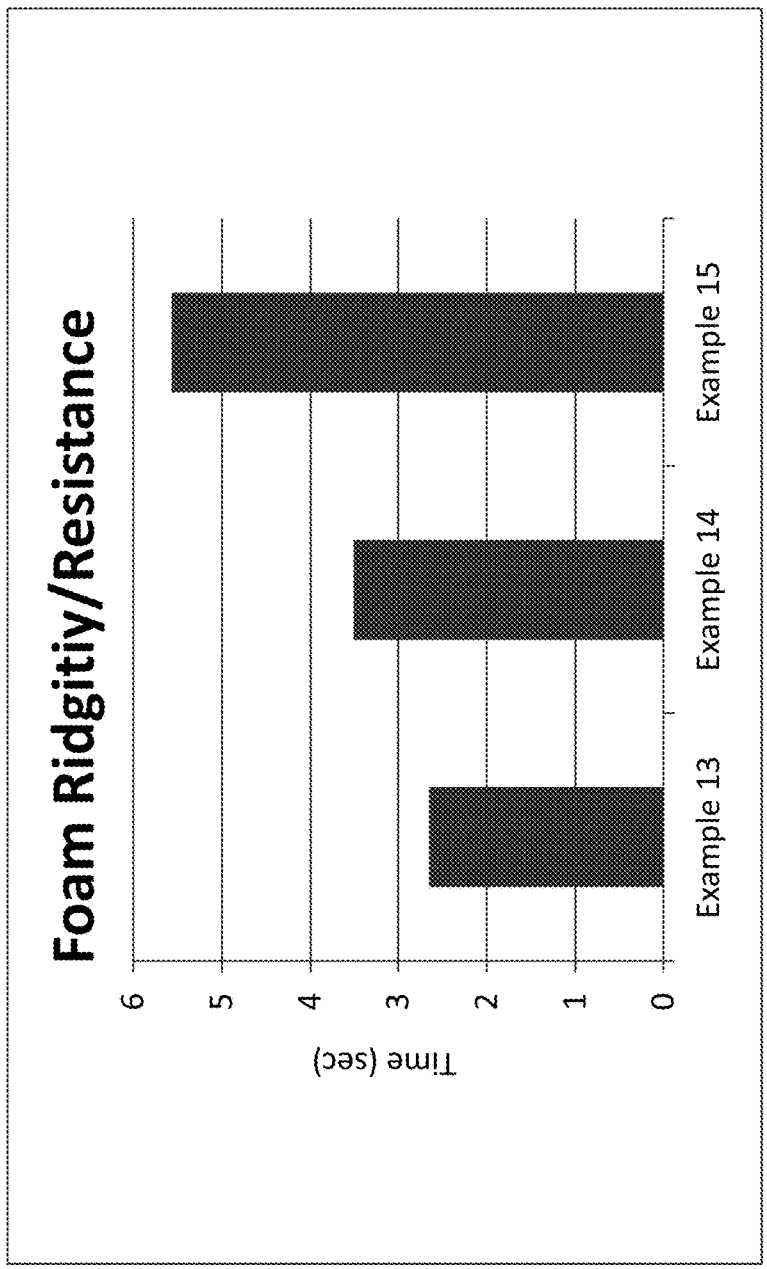
FIG. 2 is a graph showing Foam rigidity and resistance results of examples 13-15.

FIG. 2: Foam Rigidity and Resistance Results of Examples 13-15

Example 15 has the most rigid foam compare to formulation examples 13 and 14. This demonstrates that the addition of foam boosting and foam structure enhancing agents like Glyceryl Caprylate/Caprate, PEG 8000 and Hexylene Glycol and Myristamide Diisopranolamide to the cleaning composition increases foam rigidity and foam resistance thereby increasing consumer product preference.

Panel Test

The development of the Antimicrobial composition containing cationic active ingredient, cationic compatible surfactant, foam boosting agent, foam structure enhancing agent, and skin conditioning agent with optional addition of preservative, pH adjusting additive and fragrance was subjected to a panel test to determine its aesthetic acceptability to consumers.

During the first session, close to 40 applicants tested the cosmetic attributes of formulation example 13 compared to formulation example 14. Applicants were asked to wash their hands with plain soap to normalize skin between applicants, then applied soil on the hands and proceeded to wash with test products.

Figure 3:
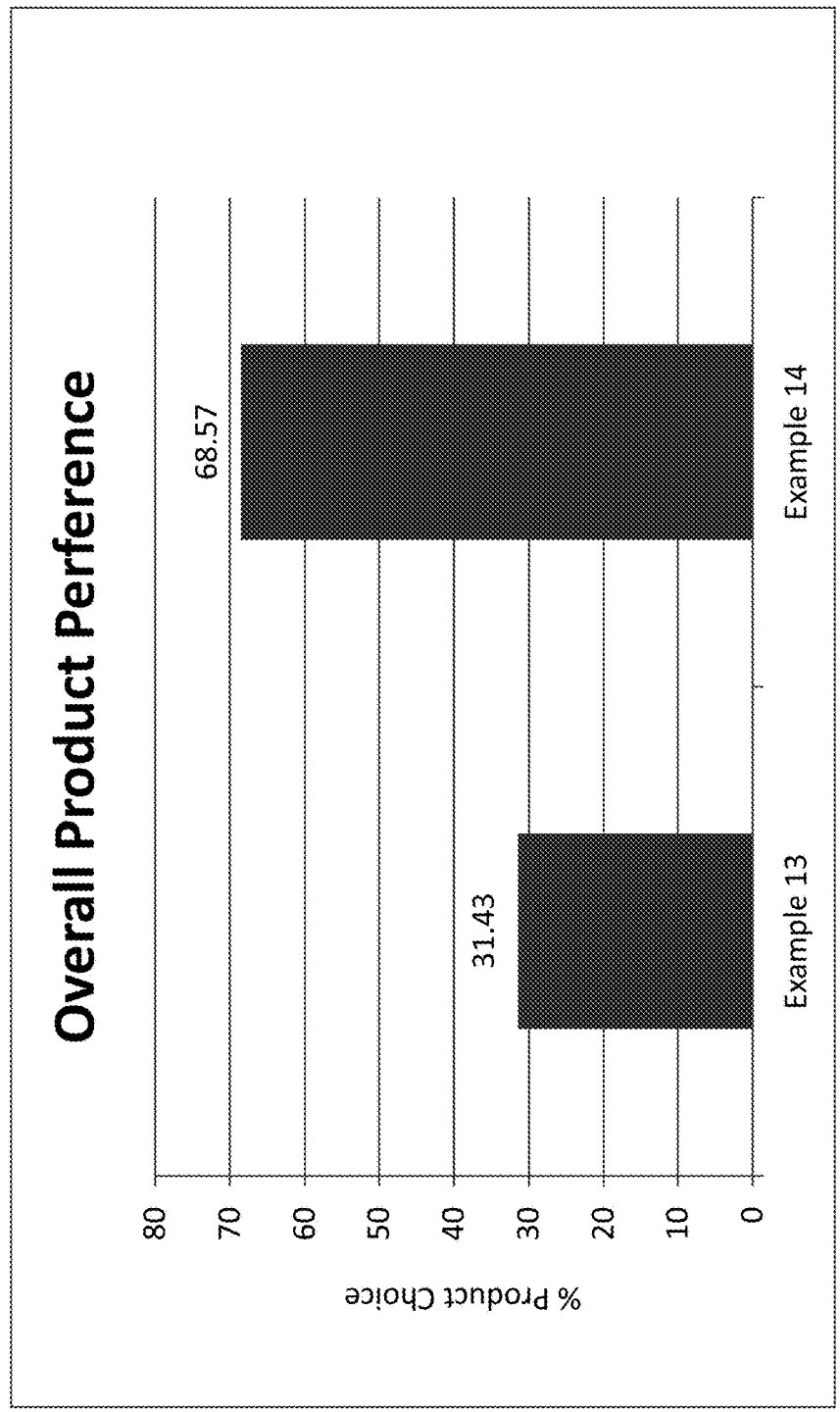
FIG. 3 is a graph showing the Panel test results of example 13 vs. example 14

FIG. 3: Panel Test Results of Example 13 vs. Example 14

The panelist preferred formulation example 14 from formulation example 13 almost by 50%. This corresponds to foam height results (table 5) and foam rigidity and resistance results (FIG. 2) where formulation 14 performed better than 13. Therefore, improved foam height and foam rigidity confirms better foam aesthetic profile that can be translated into consumer preference.

During the second session, 30 applicants tested the cosmetic attributes of formulation example 15 with unique foam boosting and foam structure enhancing agents, compared to commercially available Triclosan active foam hand soaps.

Figure 4:
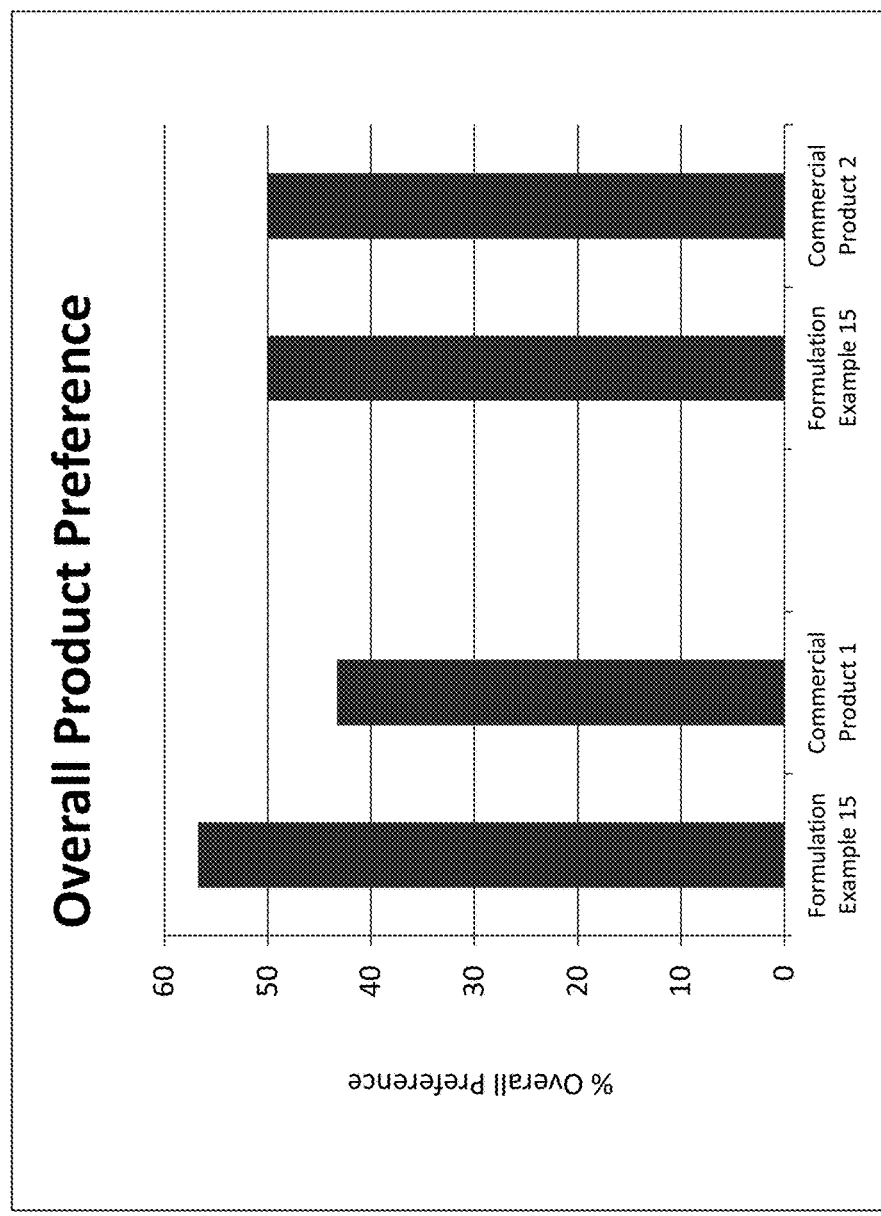
FIG. 4 is a graph showing the Panel test results of formulation example 15 vs. commercially available foam hand soaps.

FIG. 4: Panel Test Results of Formulation Example 15 vs. Commercially Available Foam Hand Soaps As seen by the results above, formulation example 15 with unique foam boosting and foam structure enhancing agents is more preferred than commercial product 1 and equally preferred to commercial product 2.

From the panel tests conducted, and results of foam height and foam rigidity we have proven that the addition of unique foam boosting and foam structure enhancing agents improve the formula aesthetic profile thereby leading to consumer acceptability while maintaining the required antimicrobial efficacy.

pH Dependence of Cationic Antimicrobial Active

Figure 5:
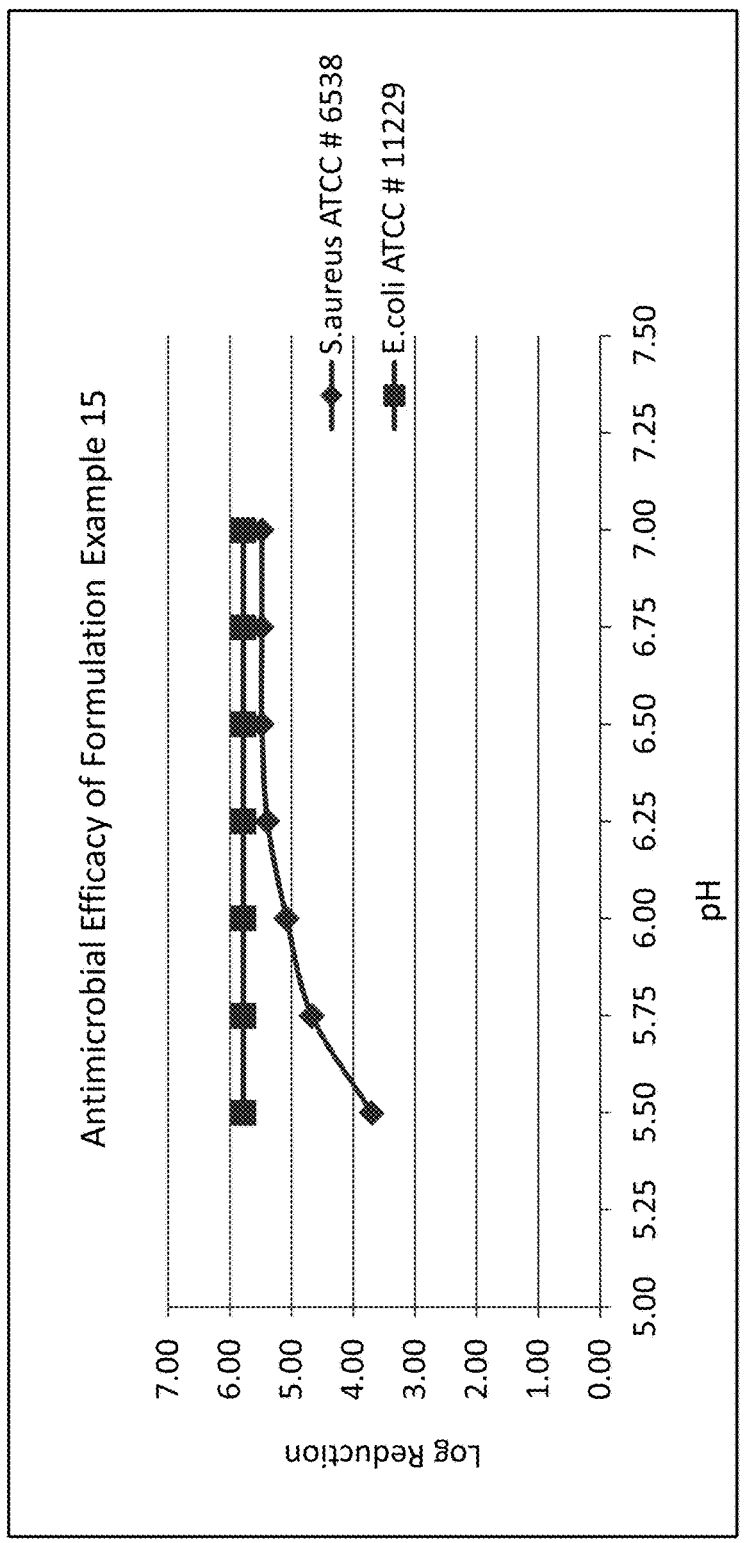
FIG. 5 is a graph showing pH range of antimicrobial efficacy of Example Formulation 15 at 30 sec exposure time

The activity of cationic antimicrobial active depends on the final pH of the cleaning composition. FIG. 5 shows the results of Antimicrobial efficacy of formulation example 15 at various pH ranges (5.50-7.0)

FIG. 5: pH Range of Antimicrobial Efficacy of Example Formulation 15 at 30 sec Exposure Time The efficacy test results show that the antimicrobial efficacy depends on the pH of the formulation. Within pH range of 5.75-7.0, the cleaning composition effectively reduces microbial populations, is phase stable, generates stable foam during the wash and is mild to skin.

Alternate Cationic Active Ingredients

TABLE 7

Antimicrobial efficacy of various cationic actives

| Active Ingredient System | Level (% w/w) | S. Aureus | E. coli | Exposure Time |
|---|---|---|---|---|
| Benzethonium Chloride | 0.65% | >5.39 | >5.73 | 30 seconds |
| Chlorohexidine Gluconate | 2% | >5.39 | >5.73 | 30 seconds |
| Chlorohexidine Gluconate | 4% | >5.39 | >5.73 | 30 seconds |
| Didecyl Dimethyl Ammonium Chloride | 0.65% | >5.39 | >5.73 | 30 seconds |
| Polyhexamethylene Biguanide | 0.65% | 3.10 | >5.73 | 30 seconds |

Table 7 illustrates efficacy of four different cationic actives formulated independently in the composition of formulation example 15 at pH 6.25. All actives have high antimicrobial activity against S. aureus and E. coli bacteria at 30 seconds exposure time.

Example 16

| Description | wt % |
|---|---|
| USP Purified Water | 75.10 |
| Benzalkonium Chloride, 50% | 0.00 |
| Lauryl Dimethylamine Oxide, 30% | 12.50 |
| Glyceryl Caprylate/Caprate | 0.25 |
| Cocamidopropyl PG Dimonium Chloride Phosphate, 47% | 2.00 |
| Polyethylene Glycol 8000 | 1.50 |
| Hexylene Glycol | 5.00 |
| Myristamide Diisopropanolamide | 0.35 |
| Phenoxyethanol | 0.40 |
| Hydroxypropyl Guar Hydroxypropyltrimonium chloride | 0.20 |
| Vitamine E Acetate | 0.10 |
| Glycerine | 1.50 |
| Methyl Glueth-20 | 0.50 |
| PEG-12 Dimethicone | 0.15 |
| Citric Acid 50% | 0.37 |
| Potassium Hydroxide, 45% | 0.05 |
| Fragrance | 0.03 |
| Total | 100.00 |

Efficacy Results of Formulation Example 16

| | S. aureus (ATCC # 6538) | Exposure Time |
|---|---|---|
| Formulation example 16 | No Log Reduction | 30 seconds |

Formulation Example 16 shows that the antimicrobial activity of S. aureus was reduced to "No detectable reduction" when the Antimicrobial Cationic biocide was removed. Therefore, one can conclude that the composition must have an antimicrobial active in order to be efficacious.

The antimicrobial compositions of the present invention have several practical end uses, including hand cleansers, surgical scrubs, hand sanitizer, and similar personal care products. Additional types of compositions include foamed compositions, such as creams, mousses, and the like. The present antimicrobial compositions can be manufactured as dilute ready-to-use compositions, or as concentrates that are diluted prior to or at the point of use. The dilution may occur manually or via automated dispensing and/or diluting equipment.

Many modifications and variations of the invention as hereinbefore set forth can be made without departing from the spirit and scope thereof, and, therefore, only such limitations should be imposed as are indicated by the appended claims.

What is claimed:

1. A foaming antimicrobial dermal cleanser comprising:
    a. a cationic active ingredient;
    b. from about 10 wt. % to about 12.5 wt. % of a cationic compatible surfactant, wherein the cationic compatible surfactant is an alkyl amine oxide and/or an alkyl ether amine oxide;
    c. from about 0.01 wt. % to about 1 wt. % of a foam boosting agent, wherein the foam boosting agent is selected from the group consisting of: glyceryl caprylate/caprate, sorbitan sesquicaprylate, phospholipids, polyethylene glycol dimethicone with methylesters, polyethylene glycol-7 glyceryl coco-ate, capris/caprylic monoglycerides, hydrophobically modified cationic polymers, and combinations thereof;
    d. from about 5 wt. % to about 8 wt. % a foam structure enhancing agent;
    e. a skin conditioning agent; and
    f. a water;
    wherein the cleanser is substantially free of anionic surfactants and triclosan.

2. The foaming antimicrobial dermal cleanser of claim 1, wherein the cleanser comprises about 0.01 wt. % to about 10 wt. % of the cationic active ingredient.

3. The foaming antimicrobial dermal cleanser of claim 1, wherein the cationic active ingredient is selected from the group consisting of: a salt of a biguanide, an organic salt of a quaternary ammonium containing compound or an inorganic salt of a quaternary ammonium containing compound, and an organic salt of chlorohexidine.

4. The foaming antimicrobial dermal cleanser of claim 1, wherein the cationic compatible surfactant component includes about 12.5 wt. % of the alkyl amine oxide and/or alkyl ether amine oxide.

5. The foaming antimicrobial dermal cleanser of claim 1, wherein the cationic compatible surfactant is lauryl dimethyl amine oxide.

6. The foaming antimicrobial dermal cleanser of claim 1, wherein the foam boosting agent comprises glyceryl caprylate/caprate.

7. The foaming antimicrobial dermal cleanser of claim 1, wherein the foam structure enhancing agent is selected from the group consisting of polyethylene glycol 8000, hexylene glycol, myristamide diisopropanolamide, phenoxyethanol, and combinations thereof.

8. The foaming antimicrobial dermal cleanser of claim 1, wherein the skin conditioning agent is selected from the group consisting of glycerin, vitamin E acetate, methyl glueth-20, hydroxypropyl guar hydroxypropyltrimonium chloride, and combinations thereof.

9. The foaming antimicrobial dermal cleanser of claim 7, wherein the foam structure enhancing agent is present in an amount of about 7 wt. % of the cleanser.

10. The foaming antimicrobial cleanser of claim 1, wherein the foam structure enhancing agent is hexylene glycol.

11. The foaming antimicrobial dermal cleanser of claim 1, wherein the foam structure enhancing agent comprises phenoxyethanol.

12. A method of reducing bacterial, microbial, fungal or viral populations on a dermal tissue of a mammal comprising the step of:
    contacting the dermal tissue of the mammal with the foaming antimicrobial dermal cleanser of claim 1 for a sufficient time to provide substantial bactericidal, microbicidal, fungicidal or virucidal reduction.

13. The method of claim 12, wherein the sufficient contact time is between about 5 to about 60 seconds.

14. The method of claim 12, wherein the foaming antimicrobial dermal cleanser is rinsed off of the dermal tissue after contact or remains on the dermal tissue after contact.

15. A foaming antimicrobial dermal cleanser comprising:
    a. a cationic active ingredient;
    b. from about 10 wt. % to about 12.5 wt. % of a cationic compatible surfactant;
    wherein the cationic compatible surfactant is an alkyl amine oxide and/or an alkyl ether amine oxide;
    c. from about 0.01 wt. % to about 1 wt. % of a foam boosting agent, wherein the foam boosting agent is selected from the group consisting of: glyceryl caprylate/caprate, sorbitan sesquicaprylate, phospholipids, polyethylene glycol dimethicone with methylesters, polyethylene glycol-7 glyceryl cocoate, capric/caprylic monoglycerides, hydrophobically modified cationic polymers, and combinations thereof;
    d. from about 5 wt. % to about 8 wt. % of a foam structure enhancing agent;
    e. a dermal adjuvant; and
    f. water;
    wherein the cleanser is substantially free of anionic surfactants, lower alcohols, and triclosan.

16. The foaming antimicrobial dermal cleanser of claim 15, wherein the foam structure enhancing agent is selected from the group consisting of polyethylene glycol 8000, hexylene glycol, myristamide diisopropanolamide, phenoxyethanol and combinations thereof.

17. The foaming antimicrobial dermal cleanser of claim 15, wherein the foam structure enhancing agent includes hexylene glycol.

18. The foaming antimicrobial dermal cleanser of claim 15, wherein the cationic compatible surfactant is lauryl dimethyl amine oxide.

19. The foaming antimicrobial dermal cleanser of claim 15, further comprising a preservative.

* * * * *